United States Patent
Hiraga et al.

(10) Patent No.: US 11,890,410 B2
(45) Date of Patent: Feb. 6, 2024

(54) INSUFFLATOR, CONNECTOR FOR INSUFFLATOR, AND INSUFFLATION APPARATUS

(71) Applicant: OLYMPUS CORPORATION, Hachioji (JP)

(72) Inventors: Kunitoshi Hiraga, Tama (JP); Koji Yamaoka, Hamura (JP); Yuma Kasuya, Hachioji (JP); Keita Kimura, Hachioji (JP); Takefumi Uesugi, Tachikawa (JP); Shinya Torii, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 670 days.

(21) Appl. No.: 16/932,292

(22) Filed: Jul. 17, 2020

(65) Prior Publication Data
US 2021/0016022 A1   Jan. 21, 2021

Related U.S. Application Data

(63) Continuation of application No. PCT/JP2018/029963, filed on Aug. 9, 2018.

(30) Foreign Application Priority Data

Feb. 6, 2018  (JP) ................................ 2018-019317

(51) Int. Cl.
  *A61M 39/10* (2006.01)
  *A61M 13/00* (2006.01)
  *A61M 39/14* (2006.01)

(52) U.S. Cl.
  CPC .......... *A61M 13/003* (2013.01); *A61M 39/14* (2013.01); *A61M 2205/3331* (2013.01); *A61M 2210/1021* (2013.01)

(58) Field of Classification Search
  CPC .................. A61M 39/00; A61M 39/10; A61M 2039/1077; A61M 5/1413; A61B 1/00064;
  (Continued)

(56) References Cited

U.S. PATENT DOCUMENTS

| 3,244,425 A | * | 4/1966 | Wilkinson | ............... F16J 15/38 |
| | | | | 277/390 |
| 5,492,147 A | * | 2/1996 | Challender | ............. F16L 37/28 |
| | | | | 604/905 |

(Continued)

FOREIGN PATENT DOCUMENTS

| JP | 2005-110978 A | 4/2005 |
| JP | 2005-245772 A | 9/2005 |

(Continued)

OTHER PUBLICATIONS

Oct. 9, 2018 International Search Report issued in International Patent Application No. PCT/JP2018/029963.

*Primary Examiner* — Laura A Bouchelle
*Assistant Examiner* — Anna E Goldberg-Richmeier
(74) *Attorney, Agent, or Firm* — Oliff PLC

(57) ABSTRACT

A connector includes a first port, a second port, a first sealing member and a second sealing member. The first port and the first pipe sleeve portion are connected with each other such that at least a part of the first port and at least a part of the first pipe sleeve portion engage with each other by fitting and overlap with each other, and a first sealing member is positioned between two overlapping portions. The second port and the second pipe sleeve portion are connected with each other such that at least a part of the second port and at least a part of the second pipe sleeve portion engage with each other by fitting and push each other, and a second sealing member is positioned between two pushing portions.

19 Claims, 9 Drawing Sheets

(58) Field of Classification Search
CPC ............ A61B 1/00066; A61B 1/00112; A61B 1/00119; A61B 1/00121; A61B 1/00128; F16L 37/00; F16L 37/22; F16L 37/23; F16L 37/02; F16L 37/025; F16L 37/04; F16L 37/05; F16L 3/01; F16L 3/22; F16L 3/221; F16L 3/222; F16L 3/237
See application file for complete search history.

(56) References Cited

U.S. PATENT DOCUMENTS

| | | | |
|---|---|---|---|
| 8,356,794 B1 * | 1/2013 | Liu | ................. F16L 37/23 |
| | | | 251/149.6 |
| 2010/0168520 A1 | 7/2010 | Poll et al. | |
| 2010/0198014 A1 | 8/2010 | Poll et al. | |
| 2011/0054256 A1 * | 3/2011 | Cushner | ............ A61B 1/00068 |
| | | | 600/156 |
| 2015/0005582 A1 | 1/2015 | Poll et al. | |
| 2015/0073214 A1 * | 3/2015 | Ueda | .................. A61B 1/121 |
| | | | 600/114 |
| 2015/0342449 A1 | 12/2015 | Poll et al. | |
| 2017/0181604 A1 * | 6/2017 | Schena | ............. A61B 1/00112 |

FOREIGN PATENT DOCUMENTS

| | | | |
|---|---|---|---|
| JP | 2012-511394 A | 5/2012 | |
| WO | 2010/068265 A1 | 6/2010 | |
| WO | 2010/068822 A2 | 6/2010 | |
| WO | WO-2016178355 A1 * | 11/2016 | ............... A61B 1/00 |

* cited by examiner

INSUFFLATOR, CONNECTOR FOR INSUFFLATOR, AND INSUFFLATION APPARATUS

CROSS REFERENCE TO RELATED APPLICATION

This application is a continuation application of PCT/JP2018/029963 filed on Aug. 9, 2018 and claims benefit of Japanese Application No. 2018-019317 filed in Japan on Feb. 6, 2018, the entire contents of which are incorporated herein by this reference.

BACKGROUND

1. Technical Field

The present disclosure relates to an insufflator, a connector for insufflator used for connecting a plurality of tubes with the insufflator and an insufflation apparatus including the insufflator and the connector for insufflator.

2. Description of the Related Art

Recently, for the purpose of alleviating invasion to a patient, laparoscopic surgery where curative treatment is performed without laparotomy has been performed. From a viewpoint that invasion to a patient is low, laparoscopic surgery is beginning to be applied to various patients and various body parts. More specifically, laparoscopic surgery is applied to an abdominal cavity, intestinum rectum or the like having a volume smaller than an average volume or to an abdominal cavity of an obese patient or the like having a volume larger than the average volume.

In laparoscopic surgery, for example, an endoscope for observation, a treatment instrument and insufflation gas are introduced into an abdominal cavity of a patient. The insufflation gas is introduced for inflating the abdominal cavity, and is used for ensuring a field of view of the endoscope and for ensuring a region for performing an operation by the treatment instrument. For example, carbon dioxide gas is used as such insufflation gas. A flow rate of the insufflation gas is controlled so as to keep a constant pressure in the cavity.

As an apparatus for feeding insufflation gas, for example, an insufflator can include a valve unit which controls a supply amount of insufflation gas and a pressure sensor provided in a supply path for the insufflation gas. A pressure in an abdominal cavity is measured by the pressure sensor in a state where the insufflation gas is supplied into the abdominal cavity intermittently and the gas feeding is stopped.

SUMMARY

According to an aspect of the present disclosure, there is provided an insufflator which includes a receptacle into which a connector to which a first tube and a second tube are connected is insertable, the receptacle being connected with the connector inserted, wherein the receptacle includes: a first pipe sleeve portion communicating with the first tube at a time of connecting the connector and the receptacle with each other; and a second pipe sleeve portion including a pipe sleeve body which is biased in a direction opposite to an insertion direction of the connector, the pipe sleeve body communicating with the second tube at the time of connecting the connector and the receptacle with each other.

According to another aspect of the present disclosure, there is provided a connector for insufflator which is insertable into a receptacle provided in an insufflator, wherein the connector for insufflator includes: a first port connected with and communicating with a first pipe sleeve portion mounted on the receptacle; a second port connected with and communicating with a second pipe sleeve portion which is provided in the receptacle and biased in a direction opposite to an insertion direction of the connector; a first sealing member providing sealing between the first port and the first pipe sleeve portion in the fitted state; and a second sealing member providing sealing between the second port and the second pipe sleeve portion in the fitted state, wherein assuming a direction parallel to an imaginary straight line orthogonal to the first end portion and the second end portion as a reference direction, the first port is connected with the first pipe sleeve portion such that at least a part of the first port extending in the reference direction and at least a part of the first pipe sleeve portion extending in the reference direction overlap with each other, the second port is connected with the second pipe sleeve portion such that at least a part of the second port and at least a part of the second pipe sleeve portion push each other in the reference direction, the first sealing member is disposed in the first port such that the first sealing member is positioned between at least a part of the first port and at least a part of the first pipe sleeve portion which overlap with each other in the fitted state, and the second sealing member is disposed in the second port such that the second sealing member is positioned between at least a part of the second port and at least a part of the second pipe sleeve portion which push each other in the fitted state.

According to yet another aspect of the present disclosure, there is provided an insufflation apparatus which includes: an insufflator including a first pipe sleeve portion, a second pipe sleeve portion and a receptacle on which the first pipe sleeve portion and the second pipe sleeve portion are mounted; a first tube and a second tube communicating with an inside of an abdominal cavity of a patient; and a connector for insufflator for connecting the first tube and the second tube with the first pipe sleeve portion and the second pipe sleeve portion, wherein the connector for insufflator includes: a connector body including a first end portion and a second end portion which are positioned on sides opposite to each other, the connector body being engageable with the receptacle by fitting; a first connecting portion and a second connecting portion disposed on a first end portion side of the connector body, wherein the first tube and the second tube are connected with the first connecting portion and the second connecting portion respectively; a first port disposed on a second end portion side of the connector body, the first port communicating with the first tube connected with the first connecting portion, the first port being connected with and communicating with the first pipe sleeve portion in a fitted state which is a state where the connector body engages with the receptacle by fitting; a second port disposed on the second end portion side of the connector body, the second port communicating with the second tube connected with the second connecting portion, the second port being connected with and communicating with the second pipe sleeve portion in the fitted state; a first sealing member providing sealing between the first port and the first pipe sleeve portion in the fitted state; and a second sealing member providing sealing between the second port and the second pipe sleeve portion in the fitted state, wherein assuming a direction parallel to an imaginary straight line orthogonal to the first end portion and the second end portion as a reference direction, the first port is connected with the first pipe sleeve portion such that at least a part of the first port extending in the reference direction and at least a part of the first pipe sleeve portion extending in the reference direction overlap with each other, and the second port is connected with the second pipe sleeve portion such that at least a part of the second port and at least a part of the second pipe sleeve portion push each other in the reference direction, the first sealing member is disposed in the first port such that the first sealing member is positioned between at least a part of the first port and at least a part of the first pipe sleeve portion which overlap with each other in the fitted state, and the second sealing member is disposed in the second port such that the second sealing member is positioned between at least a part of the second port and at least a part of the second pipe sleeve portion which push each other in the fitted state.

DETAILED DESCRIPTION OF THE PREFERRED EMBODIMENT

Hereinafter, an embodiment of the present disclosure is described with reference to drawings.
(Configuration of Endoscope System)

Figure 1:
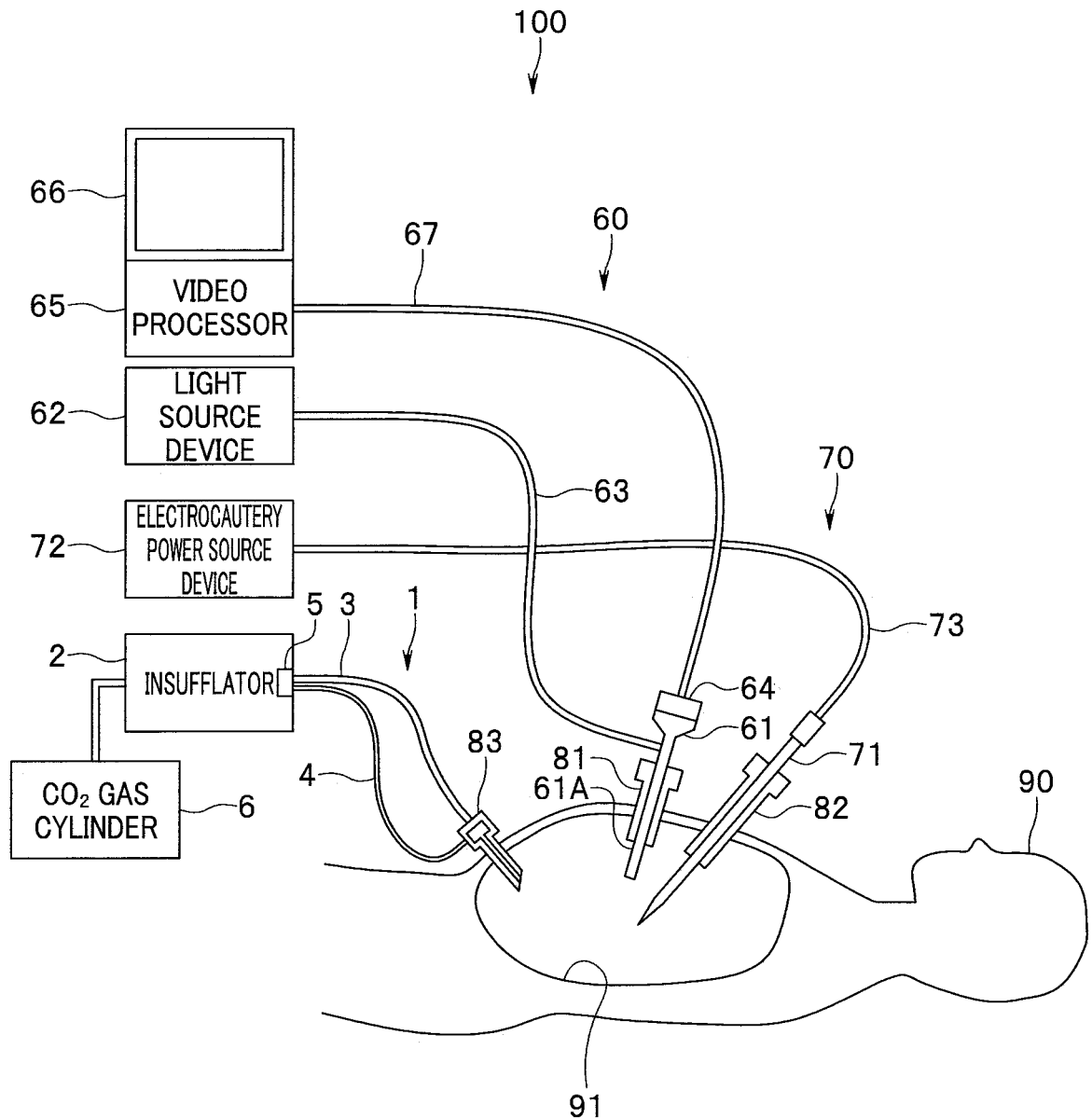
FIG. 1 is an explanatory diagram showing a configuration of an endoscope system which includes an insufflation apparatus according to an embodiment of the present disclosure.

First, with reference to FIG. 1, the configuration of an endoscope system 100 which includes an insufflation apparatus according to the embodiment of the present disclosure is described. In the embodiment, a case where an object to which surgery is applied is an affected part in an abdominal cavity 91 of a patient 90 is described as an example. As shown in FIG. 1, the endoscope system 100 mainly includes an endoscope apparatus 60, an electrocautery apparatus 70 which forms a surgical apparatus for applying a surgery to the patient 90 and the insufflation apparatus 1 according to the embodiment.

The endoscope apparatus 60 includes an endoscope 61, a light source device 62 generating illumination light supplied to the endoscope 61, a light guide cable 63 which connects the endoscope 61 and the light source device 62, an endoscope camera 64 mounted on an eyepiece portion of the endoscope 61, a video processor 65, a monitor 66 and an image pickup cable 67 which connects the endoscope camera 64 and the video processor 65.

The endoscope 61 includes an insertion portion 61A. The insertion portion 61A is inserted into the abdominal cavity 91 of the patient 90 through a trocar 81 punctured into the patient 90. The insertion portion 61A includes a light guide disposed in the insertion portion 61A, and an illumination window and an observation window positioned on a distal end of the insertion portion 61A. An illumination light generated by the light source device 62 is transmitted to a light guide cable 63 and a light guide in this order, and is irradiated to an affected part in the abdominal cavity 91 through the illumination window.

An object such as the affected part illuminated by the illumination light is formed as an optical image by an objective lens mounted on the observation window. The optical image is transmitted to the eyepiece portion. The endoscope camera 64 picks up the optical image transmitted to the eyepiece portion, and generates an image pickup signal. The image pickup signal is transmitted to the video processor 65 via the image pickup cable 67. The video processor 65 generates a video signal by applying predetermined signal processing to the image pickup signal. The monitor 66 displays the video signal generated by the video processor 65 as an endoscope image.

In place of the endoscope 61 on which the endoscope camera 64 is mounted, an endoscope which incorporates an image pickup device in a distal end portion of the insertion portion may be used.

The electrocautery apparatus 70 includes an electrocautery 71, an electrocautery power source device 72 which generates high frequency power supplied to the electrocautery 71 and a cable 73 which electrically connects the electrocautery 71 and the electrocautery power source device 72. The electrocautery 71 is inserted into the abdominal cavity 91 of the patient 90 through a trocar 82 punctured into the patient 90. A surgeon performs predetermined treatment such as cauterization by operating a switch (not shown) mounted on a grasping portion or the like of the electrocautery 71.

The insufflation apparatus 1 is an apparatus for inflating the abdominal cavity 91. The insufflation apparatus 1 supplies insufflation gas into the abdominal cavity 91 for ensuring a field of view of the endoscope 61 and for ensuring a region for performing surgery by the electrocautery 71. The insufflation apparatus 1 includes an insufflator 2 which is an apparatus body, a first tube 3 and a second tube 4 which communicate with an inside of the abdominal cavity 91 of the patient 90, a connector for insufflator (hereinafter, simply referred to as a connector) 5 according to the embodiment and a carbon dioxide gas cylinder (hereinafter, simply referred to as a gas cylinder) 6 which stores carbon dioxide as insufflation gas. The insufflator 2 includes an operation portion not shown for performing various operations and setting and a display portion not shown for displaying a pressure in the abdominal cavity 91, a flow rate of feeding gas and the like.

The connector 5 is used for connecting respective one end portions of the first and second tubes 3, 4 with the insufflator 2. The respective other end portions of the first and second tubes 3, 4 are connected with a trocar 83 punctured into the patient 90, for example. The trocar 83 has conduits which cause the first and second tubes 3, 4 and the inside of the abdominal cavity 91 to communicate with each other. The connector 5 may be a disposable-type connector.

(Configuration of Insufflator)

Hereinafter, with reference to FIG. 2, the configuration of the insufflator 2 is described in detail. The insufflator 2 includes a first pipe sleeve portion 11, a second pipe sleeve portion 12 and a receptacle 10 to which the first and second pipe sleeve portions 11, 12 are connected. A connector body of the connector 5 described later engages with the receptacle 10 by fitting. The connector 5 is used for connecting the first and second tubes 3, 4 with the first and second pipe sleeve portions 11, 12. The first tube 3 is connected with the first pipe sleeve portion 11 by way of the connector 5. The second tube 4 is connected with the second pipe sleeve portion 12 by way of the connector 5. In the embodiment, the first tube 3 is provided for supplying insufflation gas into the abdominal cavity 91 of the patient 90 (see FIG. 1). The second tube 4 is provided for transmitting a pressure in the abdominal cavity 91 of the patient 90. The configuration of the receptacle 10 and the configurations of the first and second pipe sleeve portions 11, 12 are described in detail later.

The insufflator 2 further includes a gas feeding conduit 13. One end of the gas feeding conduit 13 is connected with the first pipe sleeve portion 11. The other end of the gas feeding conduit 13 is connected with the gas cylinder 6. The gas feeding conduit 13 is a conduit for introducing insufflation gas (carbon dioxide) in the gas cylinder 6 into the first pipe sleeve portion 11.

The insufflator 2 further includes a pressure reducer 14, a flow rate/pressure regulator 15, a pressure sensor 16, a flow rate sensor 17 and an electromagnetic valve 18 on an intermediate portion of the gas feeding conduit 13 in this order from a gas cylinder 6 side. The pressure reducer 14 reduces a pressure of insufflation gas fed from the gas cylinder 6. The flow rate/pressure regulator 15 regulates a flow rate and the pressure of the pressure-reduced insufflation gas. The pressure sensor 16 measures the pressure of the insufflation gas regulated by the flow rate/pressure regulator 15. The flow rate sensor 17 measures the flow rate of the insufflation gas regulated by the flow rate/pressure regulator 15. The electromagnetic valve 18 opens or closes the gas feeding conduit 13.

The insufflator 2 further includes a pressure sensor 20 and a pressure measurement conduit 19 which communicates with the pressure sensor 20. One end of the pressure measurement conduit 19 is connected with the second pipe sleeve portion 12. The other end of the pressure measurement conduit 19 is connected with the pressure sensor 20. The pressure measurement conduit 19 is a conduit through which a pressure in the abdominal cavity 91 of the patient 90 transmitted to the second pipe sleeve portion 12 through the second tube 4 is transmitted to the pressure sensor 20. The pressure sensor 20 measures the pressure in the abdominal cavity 91 of the patient 90 transmitted through the pressure measurement conduit 19.

The insufflator 2 further includes a control board 21 and a power source 22. The control board 21 is electrically connected with the flow rate/pressure regulator 15, the pressure sensor 16, the flow rate sensor 17, the electromagnetic valve 18 and the pressure sensor 20 via signal lines. The power source 22 is electrically connected with the flow rate/pressure regulator 15, the pressure sensor 16, the flow rate sensor 17, the electromagnetic valve 18, the pressure sensor 20 and the control board 21 via power source lines.

The control board 21 includes a central processing unit (hereinafter, referred to as CPU) not shown which controls the flow rate/pressure regulator 15 and the electromagnetic valve 18 based on operation contents and set values inputted to the operation portion not shown and a measured value of the pressure sensor 20. The CPU controls the flow rate/pressure regulator 15 such that a pressure in the abdominal cavity 91 of the patient 90 agrees with a set value, and controls starting and stopping the supply of insufflation gas by controlling the electromagnetic valve 18. The CPU can also control a flow rate and a pressure of insufflation gas based on a measured value of the pressure sensor 16 and a measured value of the flow rate sensor 17.

The control board 21 may further include a memory unit for storing operation contents and set values inputted to the operation portion not shown. In this case, the CPU may control the flow rate/pressure regulator 15 and the electromagnetic valve 18 based on the contents stored in the memory unit.

(Configuration of Connector)

Figure 2:
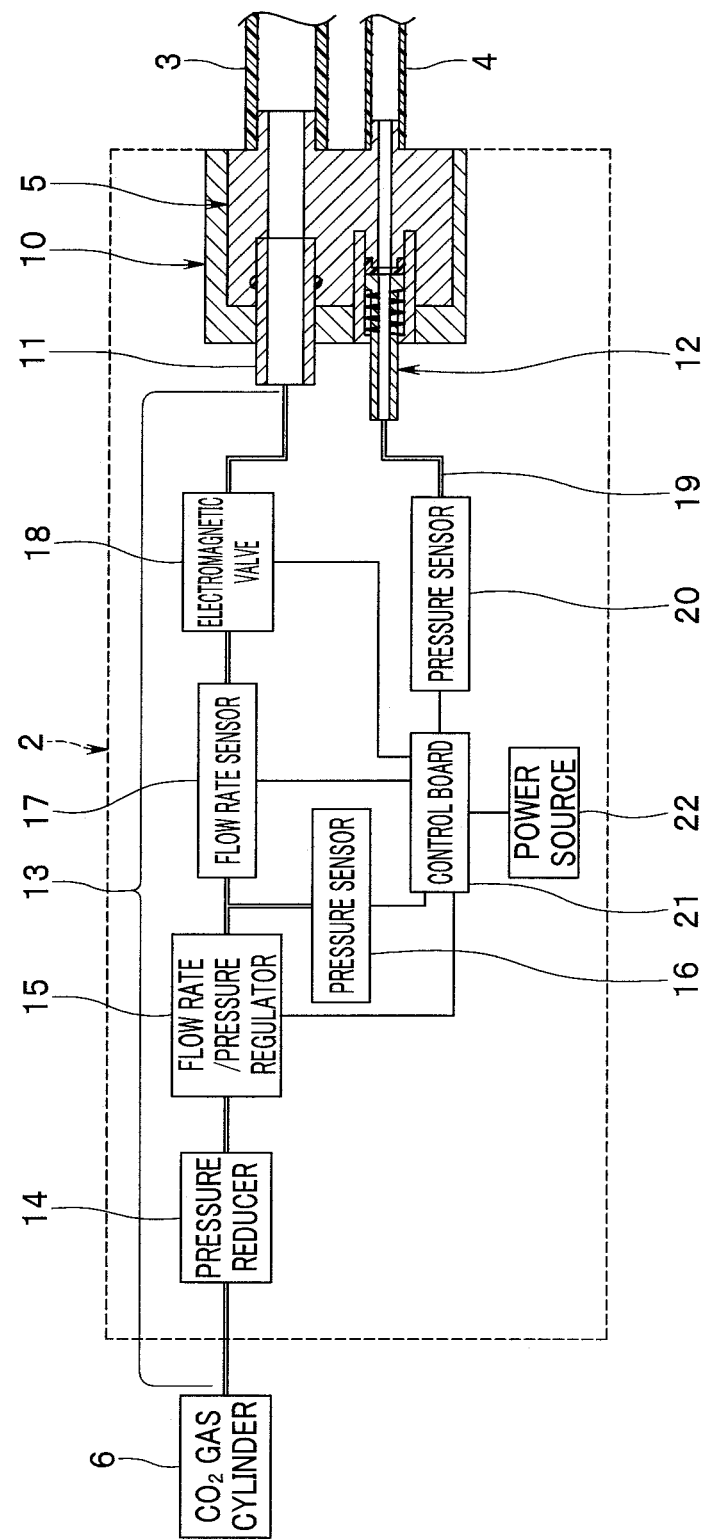
FIG. 2 is an explanatory diagram showing a configuration of an insufflator in the embodiment of the present disclosure.
Figure 3:
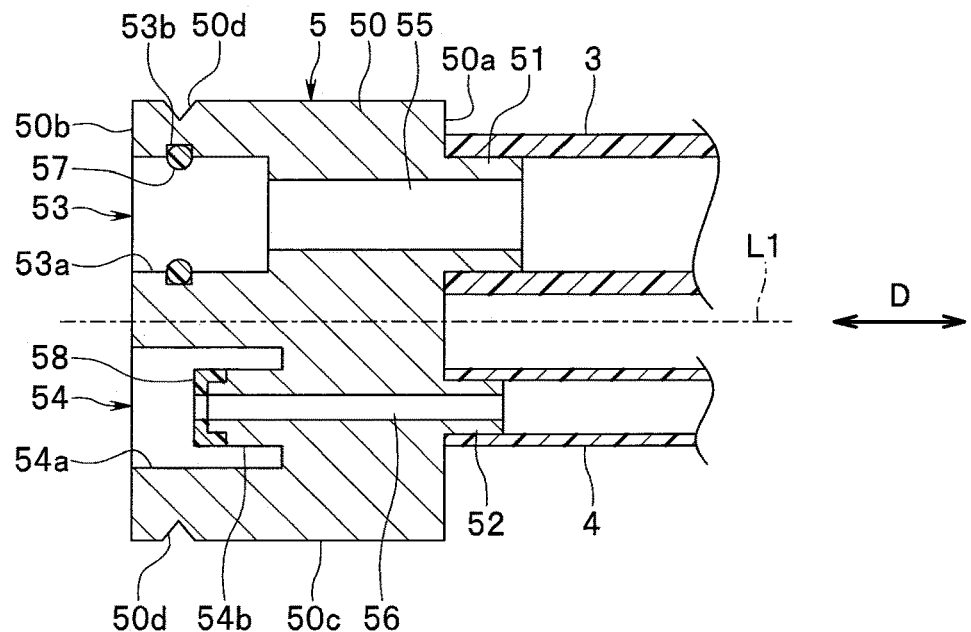
FIG. 3 is a cross-sectional view of a connector according to the embodiment of the present disclosure.
Figure 4:
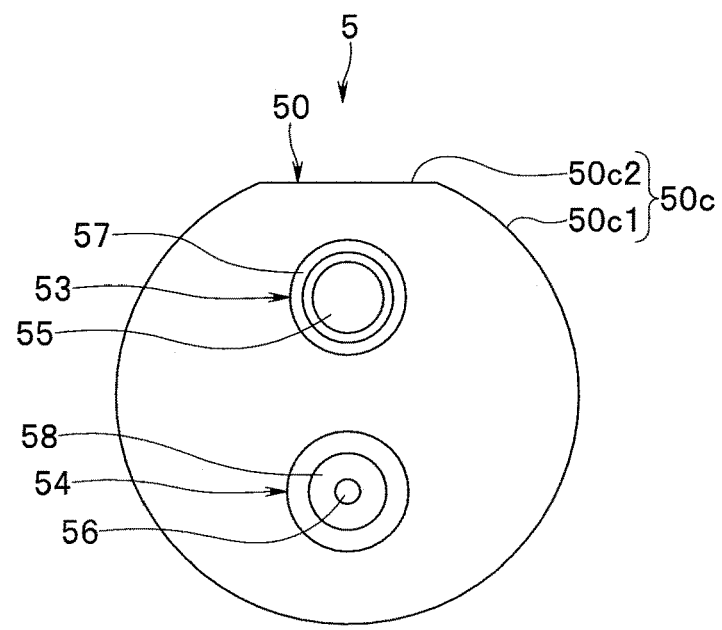
FIG. 4 is a front view of the connector shown in FIG. 3.

Next, with reference to FIG. 3 and FIG. 4, the configuration of the connector 5 according to the embodiment is described in detail. FIG. 3 is a cross-sectional view of the connector 5. FIG. 4 is a front view of the connector 5 shown in FIG. 3. The connector 5 includes the connector body 50 engaging with the receptacle 10 by fitting (see FIG. 2). Hereinafter, a state where the connector body 50 engages with the receptacle 10 by fitting is referred to as a fitted state. The connector body 50 may be made of a metal material, a resin material, or a combination of a metal material and a resin material. FIG. 3 shows an example where the connector body 50 is made of a metal material.

As shown in FIG. 3, the connector body 50 includes a first end portion 50a and a second end portion 50b which are positioned on sides opposite to each other, and an outer peripheral surface 50c which connects the first end portion 50a and the second end portion 50b. FIG. 4 shows the connector 5 as viewed from a second end portion 50b side. In the embodiment, as shown in FIG. 3, a reference direction D is defined. The reference direction D is a direction parallel to an imaginary straight line L1 which intersects with the first and second end portions 50a, 50b.

In the embodiment, a shape of a cross section of the connector body 50 orthogonal to the reference direction D is approximately D shape. As shown in FIG. 4, the outer peripheral surface 50c of the connector body 50 includes a curved surface portion 50c1 and a flat surface portion 50c2. A shape of the cross section of the connector body 50 is not limited to such a D shape, and may be a circular shape, an elliptical shape, a polygonal shape or the like, and the shape of the cross section of the connector body 50 may differ corresponding to a position in the reference direction D.

As shown in FIG. 3, the connector body 50 further includes a support groove 50d formed on the outer peripheral surface 50c in a circumferential direction about an axis of the connector body 50. A locking member of the receptacle 10 described later engages with the support groove 50d by fitting. The circumferential direction about the axis of the connector body 50 means the direction about a center axis of the connector body 50. The center axis of the connector body 50 is parallel to the imaginary straight line L1 and the reference direction D.

The connector 5 further includes: a first connecting portion 51 and a second connecting portion 52 disposed on a first end portion 50a side of the connector body 50; and a first port 53 and a second port 54 disposed on the second end portion 50b side of the connector body 50. The first port 53 is disposed at the position where the first pipe sleeve portion 11 is connected with the first port 53 in a fitted state, and the second port 54 is disposed at the position where the second pipe sleeve portion 12 is connected with the second port 54 in a fitted state. In the example shown in FIG. 3 and FIG. 4, the first port 53 and the second port 54 are arranged side by side in the direction orthogonal to the reference direction D (vertical direction in FIG. 3 and FIG. 4).

In a case where the positions of the first pipe sleeve portion 11 and the second pipe sleeve portion 12 differ from the positions of the first pipe sleeve portion 11 and the second pipe sleeve portion 12 in an example shown in FIG. 6 and FIG. 7 described later, the positions of the first port 53 and the second port 54 are changed in conformity with the positions of the first pipe sleeve portion 11 and the second pipe sleeve portion 12.

The first and second connecting portions 51, 52 each protrude from the first end portion 50a. The first tube 3 is connected with the first connecting portion 51 by insertion fitting. The second tube 4 is connected with the second connecting portion 52 by insertion fitting.

As shown in FIG. 3, in the embodiment, the first port 53 is a groove-shaped portion which is formed on the second end portion 50b of the connector body 50 by cutting. The first port 53 has a shape extending in the reference direction D. A shape of a cross section of the first port 53 orthogonal to the reference direction D is a circular shape. The first port 53 has: an inner peripheral surface 53a having a center axis parallel to the reference direction D; and a groove portion 53b formed on the inner peripheral surface 53a in a circumferential direction about the center axis.

The first port 53 is not limited to the above-mentioned groove-shaped portion, and may be formed of a sleeve-like part which is fixed to the second end portion 50b side.

As shown in FIG. 3, in the embodiment, the second port 54 includes: a groove portion 54a formed on the second end portion 50b of the connector body 50 by cutting; and a protruding portion 54b protruding from a bottom portion of the groove portion 54a such that the protruding portion 54b extends in the reference direction D. The groove portion 54a has a shape extending in the reference direction D. A shape of a cross section of the groove portion 54a orthogonal to the reference direction D is a circular shape. A shape of the protruding portion 54b is a circular columnar shape extending in the reference direction D. A stepped portion to which a second sealing member described later is attached is formed on a distal end of the protruding portion 54b. The stepped portion is not an indispensable configurational element of the protruding portion 54b, and may not be formed.

The second port 54 is not limited to the above-mentioned configuration, and may be formed of: the protruding portion 54b; and a sleeve-like part fixed to the second end portion 50b side and in which the protruding portion 54b is disposed.

The connector 5 further includes: a first conduit 55 which causes the first port 53 and the first tube 3 connected with the first connecting portion 51 to communicate with each other; and a second conduit 56 which causes the second port 54 and the second tube 4 connected with the second connecting portion 52 to communicate with each other. One end of the first conduit 55 opens at a bottom portion of the first port 53, and the other end of the first conduit 55 opens at a distal end of the first connecting portion 51. With such a configuration, the first port 53 communicates with the first tube 3. One end of the second conduit 56 opens at a distal end of the protruding portion 54b of the second port 54, and the other end of the second conduit 56 opens at a distal end of the second connecting portion 52. With such a configuration, the second port 54 communicates with the second tube 4.

In a fitted state, the first port 53 is connected with and communicates with the first pipe sleeve portion 11 (see FIG. 2), and the second port 54 is connected with and communicates with the second pipe sleeve portion 12 (see FIG. 2). The connector 5 further includes: a first sealing member 57 providing sealing between the first port 53 and the first pipe sleeve portion 11 in a fitted state; and a second sealing member 58 providing sealing between the second port 54 and the second pipe sleeve portion 12 in a fitted state.

The first sealing member 57 is disposed in the first port 53. More specifically, the first sealing member 57 has an annular shape, and a part of the first sealing member 57 is accommodated in the groove portion 53b of the first port 53. A remaining portion of the first sealing member 57 is exposed to a space surrounded by the inner peripheral surface 53a of the first port 53. The first sealing member 57 is made of an elastically deformable material. As the elastically deformable material, for example, a resin material such as rubber is used. In the embodiment, particularly, the first sealing member 57 is an O-shaped ring.

The second sealing member 58 is disposed in the second port 54. More specifically, the second sealing member 58 is disposed on the distal end of the protruding portion 54b of the second port 54, and is used as a gasket. The second sealing member 58 is made of an elastically deformable material. As the elastically deformable material, for example, a resin material such as rubber is used.

Figure 5:
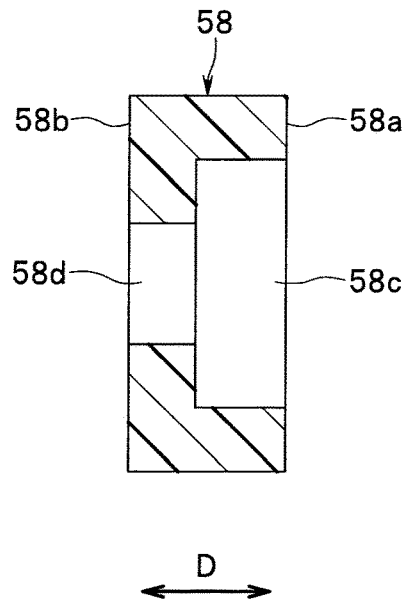
FIG. 5 is a cross-sectional view of a second sealing member in the embodiment of the present disclosure.

With reference to FIG. 5, a shape of the second sealing member 58 is described in detail. FIG. 5 is a cross-sectional view of the second sealing member 58. An external shape of the second sealing member 58 is a circular columnar shape extending in the reference direction D. The second sealing member 58 has: a first surface 58a and a second surface 58b which are directed toward sides opposite to each other; a fitting hole 58c which opens in the first surface 58a; and a ventilation hole 58d which is continuously formed with the fitting hole 58c and opens in the second surface 58b. The second sealing member 58 is attached to the protruding portion 54b by fitting the stepped portion formed on the distal end of the protruding portion 54b (see FIG. 3) into the fitting hole 58c. The ventilation hole 58d communicates with the second conduit 56 (see FIG. 3) in a state where the second sealing member 58 is attached to the protruding portion 54b.

(Configuration of Receptacle and Configurations of First and Second Pipe Sleeve Portions)

Figure 6:
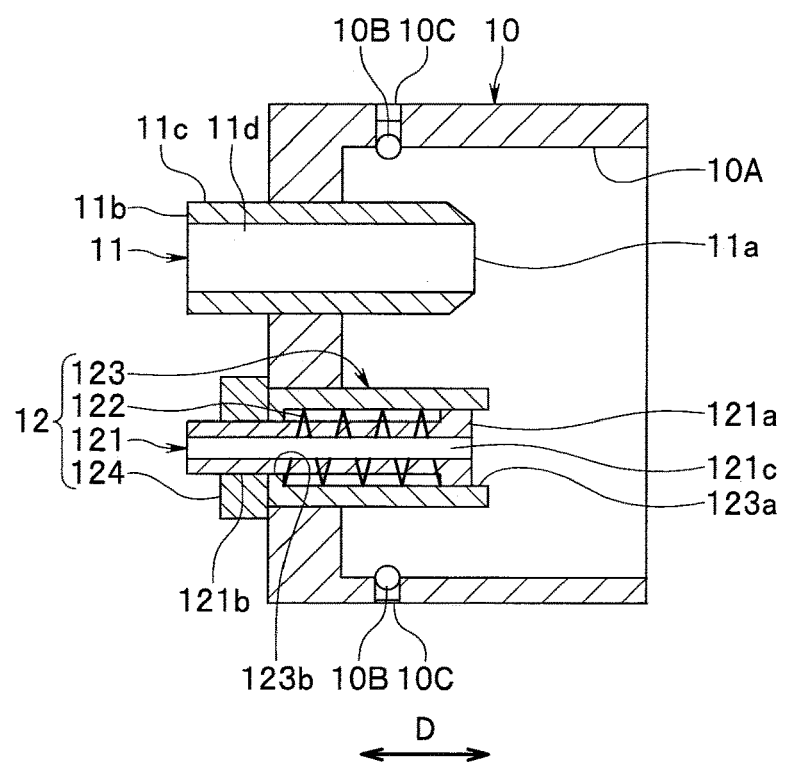
FIG. 6 is a cross-sectional view of a receptacle and first and second pipe sleeve portions in the embodiment of the present disclosure.
Figure 7:
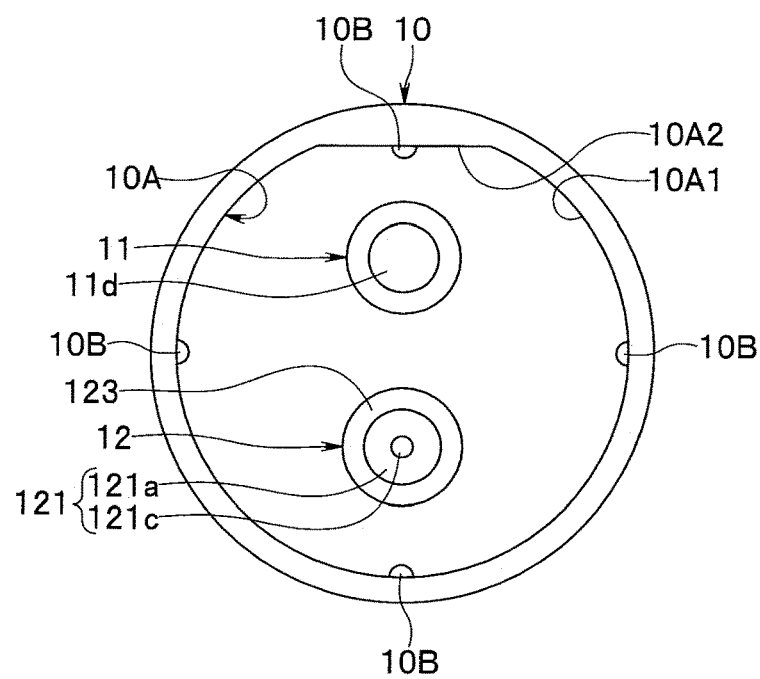
FIG. 7 is a front view of the receptacle and the first and second pipe sleeve portions shown in FIG. 6.

Next, with reference to FIG. 6 and FIG. 7, the configuration of the receptacle 10 and the configurations of the first and second pipe sleeve portions 11, 12 are described in detail. FIG. 6 is a cross-sectional view of the receptacle 10 and the first and second pipe sleeve portions 11, 12. FIG. 7 is a front view of the receptacle 10 and the first and second pipe sleeve portions 11, 12 shown in FIG. 6. Hereinafter, using a posture of the receptacle 10 in a fitted state as a reference, the configuration of the receptacle 10 and the configurations of the first and second pipe sleeve portions 11, 12 are described. A definition of the reference direction D shown in FIG. 6 is the same as the definition of the reference direction D shown in FIG. 3.

In the example shown in FIG. 6 and FIG. 7, the first pipe sleeve portion 11 and the second pipe sleeve portion 12 are mounted on the receptacle 10 such that the first pipe sleeve portion 11 and the second pipe sleeve portion 12 are arranged side by side in the direction orthogonal to the reference direction D (vertical direction in FIG. 6 and FIG. 7). However, an arrangement of the first pipe sleeve portion 11 and the second pipe sleeve portion 12 is not limited to an example shown in FIG. 6 and FIG. 7. For example, the first pipe sleeve portion 11 and the second pipe sleeve portion 12 may be arranged side by side in the lateral direction in FIG. 7, or may be arranged side by side in a direction inclined with respect to each of the vertical direction and the lateral direction in FIG. 7.

The receptacle 10, the first pipe sleeve portion 11 and the second pipe sleeve portion 12 may each be made of a metal material, a resin material or a combination of a metal material and a resin material. FIG. 6 shows an example where all of the receptacle 10, the first pipe sleeve portion 11 and the second pipe sleeve portion 12 are made of a metal material.

The receptacle 10 has a fitting hole 10A into which the connector body 50 is inserted. The fitting hole 10A has a shape which corresponds to a shape of the connector body 50. In the embodiment, a shape of a cross section of the fitting hole 10A orthogonal to the reference direction D is approximately D shape. As shown in FIG. 7, an inner peripheral surface of the fitting hole 10A has a curved surface portion 10A1 and a flat surface portion 10A2.

The receptacle 10 further includes at least one locking member which locks the connector body 50, and has at least one locking member hole. In the example shown in FIG. 6 and FIG. 7, four locking members 10B are arranged at a predetermined interval in the circumferential direction about the axis of the receptacle 10. The locking members 10B are inserted and fixed to the locking member holes 10C such that distal end portions of the locking members 10B protrude into the fitting hole 10A. As the locking member 10B, for example, a ball plunger is used. The circumferential direction about the axis of the receptacle 10 means a direction about the center axis of the receptacle 10. The center axis of the receptacle 10 is parallel to the reference direction D.

At least a part of the first pipe sleeve portion 11 has a cylindrical shape extending in the reference direction D. In the embodiment, the entire first pipe sleeve portion 11 has the cylindrical shape. The first pipe sleeve portion 11 includes: a first end portion 11a and a second end portion 11b which are positioned on sides opposite to each other; an outer peripheral surface 11c; and a conduit 11d which opens at each of the first and second end portions 11a, 11b. The first pipe sleeve portion 11 is fixed to the receptacle 10 such that the first end portion 11a and at least a part of the outer peripheral surface 11c are positioned in the fitting hole 10A. The conduit 11d communicates with the fitting hole 10A and the gas feeding conduit 13 (see FIG. 2).

The second pipe sleeve portion 12 includes: a pipe sleeve body 121 movably disposed in the reference direction D; a biasing member 122 applying a biasing force to the pipe sleeve body 121 in the reference direction D; an accommodating member 123 accommodating the pipe sleeve body 121 and the biasing member 122; and a removal preventing member 124. As shown in FIG. 6, in the embodiment, the biasing member 122 is formed of a spring, more specifically, a coil spring.

The pipe sleeve body 121 includes: a flange portion 121a; a tubular portion 121b extending from the flange portion 121a in the reference direction D; and a conduit 121c penetrating the pipe sleeve body 121 in the reference direction D. Shapes of cross sections of the flange portion 121a and the tubular portion 121b orthogonal to the reference direction D each are a circular shape. An outer diameter of the flange portion 121a is larger than an outer diameter of the tubular portion 121b. The conduit 121c opens at respective end portions of the flange portion 121a and the tubular portion 121b, and communicates with the fitting hole 10A and the pressure measurement conduit 19 (see FIG. 2).

The accommodating member 123 has a cylindrical shape extending in the reference direction D, and the accommodating member 123 is fixed to the receptacle 10 such that a part of the accommodating member 123 is positioned in the fitting hole 10A. The accommodating member 123 has: an accommodating hole 123a communicating with the fitting hole 10A; and a passing hole 123b communicating with the accommodating hole 123a and the outside of the receptacle 10. The pipe sleeve body 121 is inserted into the accommodating hole 123a and the passing hole 123b. An inner diameter of the accommodating hole 123a is slightly larger than an outer diameter of the flange portion 121a. With such a configuration, the pipe sleeve body 121 is movable in the reference direction D in the accommodating hole 123a. Although an inner diameter of the passing hole 123b is slightly larger than the outer diameter of the tubular portion 121b, the inner diameter of the passing hole 123b is smaller than the outer diameter of the flange portion 121a. Accordingly, although the tubular portion 121b can pass through the passing hole 123b, the flange portion 121a cannot pass through the passing hole 123b. Between the accommodating hole 123a and the passing hole 123b, a stepped portion formed by a difference in respective inner diameters of the accommodating hole 123a and the passing hole 123b exists.

As shown in FIG. 6, the biasing member 122 (coil spring) is accommodated in the accommodating hole 123a of the accommodating member 123, and is sandwiched between the flange portion 121a of the pipe sleeve body 121 and the stepped portion of the accommodating member 123. The tubular portion 121b of the pipe sleeve body 121 is inserted into the biasing member 122 (coil spring).

The removal preventing member 124 is fixed to the tubular portion 121b of the pipe sleeve body 121 outside the receptacle 10. The removal preventing member 124 has a function of preventing a removal of the pipe sleeve body 121 from the accommodating member 123.

(Fitted State)

Figure 8:
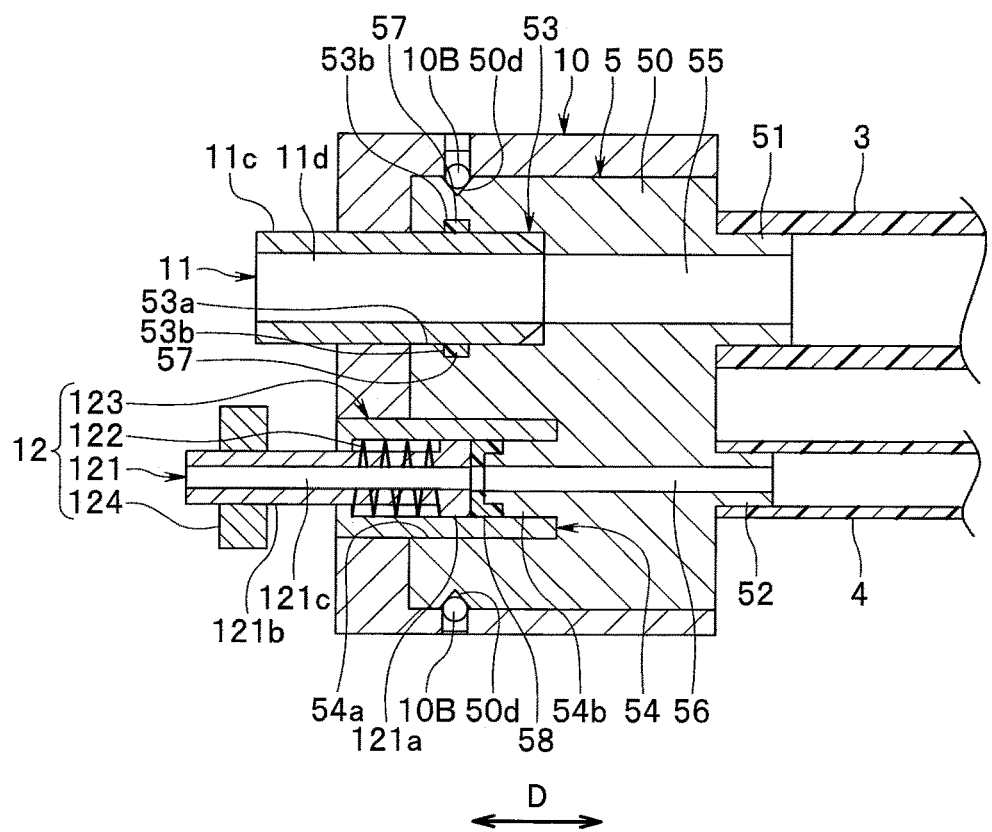
FIG. 8 is a cross-sectional view showing a state where the connector according to the embodiment of the present disclosure engages with the receptacle by fitting.
Figure 9:
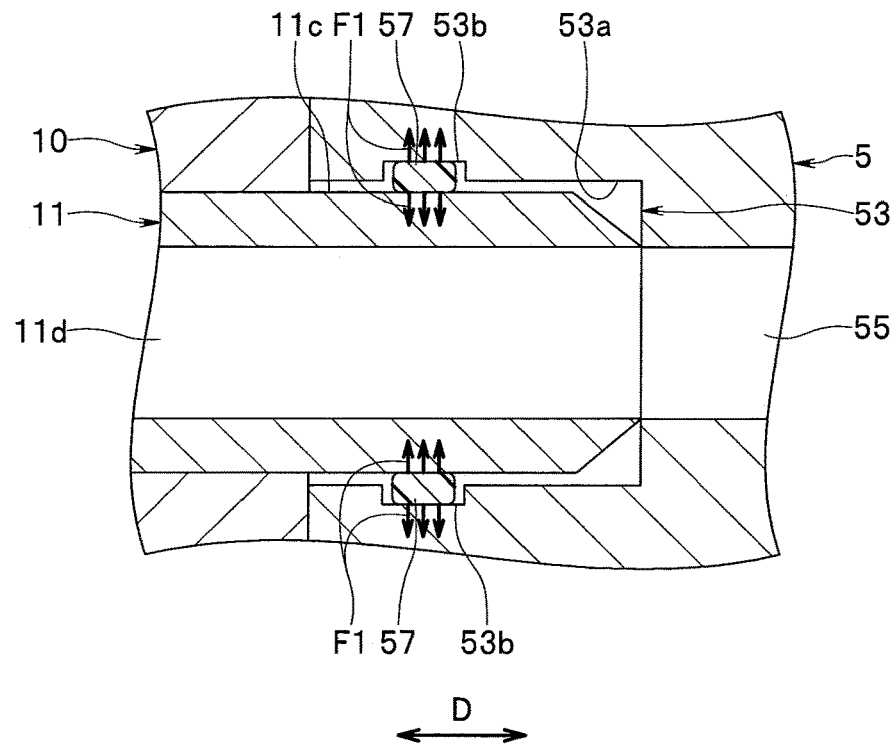
FIG. 9 is a cross-sectional view of a first port, a first sealing member and the first pipe sleeve portion in a state shown in FIG. 8.
Figure 10:
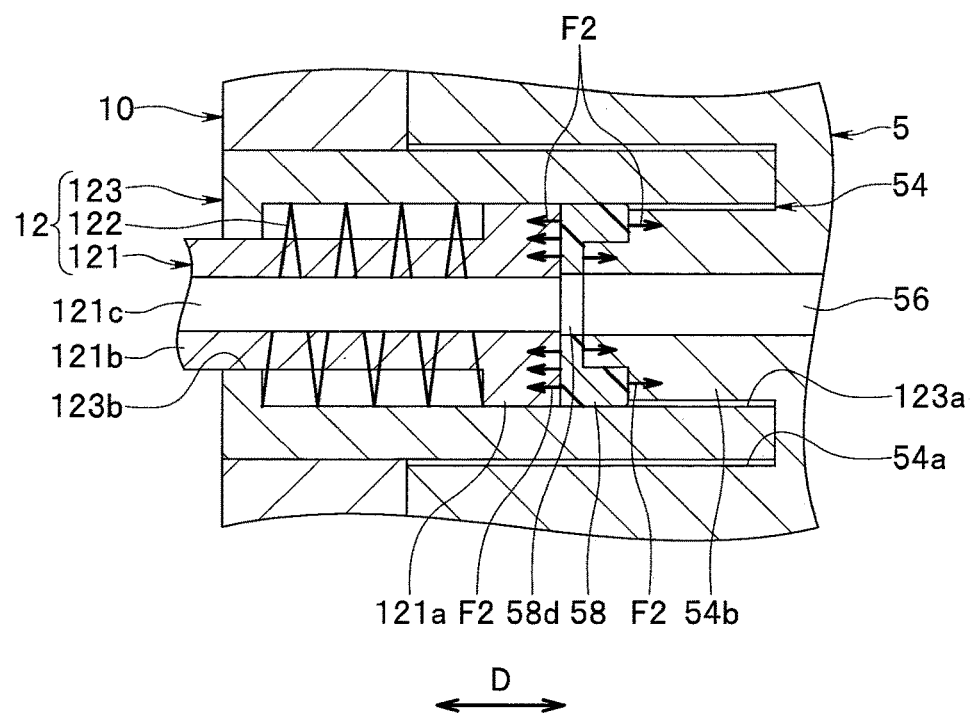
FIG. 10 is a cross-sectional view of a second port, the second sealing member and the second pipe sleeve portion in the state shown in FIG. 8.

Next, with reference to FIG. 4 and FIG. 7 to FIG. 10, a fitted state which is a state where the connector body 50 engages with the receptacle 10 by fitting is described. FIG. 8 is a cross-sectional view showing the fitted state. FIG. 9 is a cross-sectional view of the first port 53, the first sealing member 57 and the first pipe sleeve portion 11 in the fitted state. FIG. 10 is a cross-sectional view of the second port 54, the second sealing member 58 and the second pipe sleeve portion 12 in the fitted state.

In fitting the connector body 50 into the receptacle 10, the connector body 50 is inserted into the fitting hole 10A in a posture where the flat surface portion 50c2 of the outer peripheral surface 50c of the connector body 50 (see FIG. 4) agrees with the flat surface portion 10A2 of the inner peripheral surface of the fitting hole 10A of the receptacle 10 (see FIG. 7). As shown in FIG. 8, the connector body 50 is inserted into the receptacle 10 until the connector body 50 reaches a position where distal end portions of the locking members 10B are fitted into the support grooves 50d of the connector body 50. Accordingly, the connector body 50 is fitted into the receptacle 10.

The flat surface portions 10A2, 50c2 have a function of determining the posture of the connector body 50 with respect to the receptacle 10. The locking members 10B lock the connector body 50 thus performing a function of preventing removal of the connector body 50 from the receptacle 10. The flat surface portions 10A2, 50c2, the locking members 10B and the support grooves 50d are not indispensable configurational elements of the receptacle 10 and the connector body 50 and may not be provided.

The first port 53 is connected with and communicates with the first pipe sleeve portion 11 in the following manner. As shown in FIG. 8 and FIG. 9, in a fitted state, the first port 53 is connected with the first pipe sleeve portion 11 such that at least a part of the first port 53 extending in the reference direction D and at least a part of the first pipe sleeve portion 11 extending in the reference direction D overlap with each other. In the embodiment, an outer diameter of the first pipe sleeve portion 11 is smaller than an inner diameter of the first port 53 so as to allow an insertion of the first pipe sleeve portion 11 into the first port 53. In the embodiment, substantially the entire first port 53 and a portion of the first pipe sleeve portion 11 positioned in the fitting hole 10A overlap with each other in the reference direction D.

The first port 53 and the first pipe sleeve portion 11 communicate with each other when the first port 53 is connected with the first pipe sleeve portion 11. An opening of the first conduit 55 of the connector 5 and an opening of the conduit 11d of the first pipe sleeve portion 11 are formed such that the position of the opening of the first conduit 55 and the position of the opening of the conduit 11d substantially agree with each other in a fitted state.

By connecting the first port 53 and the first pipe sleeve portion 11 and causing the first port 53 and the first pipe sleeve portion 11 to communicate with each other, a first path is formed. The first path is a path for supplying insufflation gas into the abdominal cavity 91 of the patient 90 (see FIG. 1). The gas feeding conduit 13 shown in FIG. 2 forms a part of the first path, and supplies insufflation gas. The first tube 3 forms another part of the first path.

The second port 54 is connected with and communicates with the second pipe sleeve portion 12 in the following manner. As shown in FIG. 8 and FIG. 10, the second port 54 is connected with the second pipe sleeve portion 12 such that at least a part of the second port 54 and at least a part of the second pipe sleeve portion 12 push each other in the reference direction D. In the embodiment, in fitting the connector body 50 into the receptacle 10, an outer diameter of the accommodating member 123 is smaller than an inner diameter of the groove portion 54a, and an outer diameter of the protruding portion 54b is smaller than the inner diameter of the accommodating hole 123a so as to allow an insertion of the accommodating member 123 of the second pipe sleeve portion 12 into the groove portion 54a of the second port 54 and an insertion of the protruding portion 54b of the second port 54 into the accommodating hole 123a of the accommodating member 123.

In fitting the connector body 50 into the receptacle 10, the second sealing member 58 is also inserted into the accommodating hole 123a of the accommodating member 123. Accordingly, an outer diameter of the second sealing member 58 is smaller than the inner diameter of the accommodating hole 123a.

The protruding portion 54b inserted into the accommodating hole 123a pushes the pipe sleeve body 121 of the second pipe sleeve portion 12. When the pipe sleeve body 121 is pushed, a biasing force is applied to the pipe sleeve body 121 by a restoring force of the biasing member 122 in a direction opposite to a direction that the pipe sleeve body 121 is pushed. As a result, the protruding portion 54b receives a repulsive force in the direction opposite to the direction that the pipe sleeve body 121 is pushed by the protruding portion 54b. In this manner, the protruding portion 54b and the pipe sleeve body 121 are connected with each other such that the protruding portion 54b and the pipe sleeve body 121 push each other.

The second port 54 and the second pipe sleeve portion 12 communicate with each other when the second port 54 is connected with the second pipe sleeve portion 12. An opening of the second conduit 56 of the connector 5 and an opening of the conduit 121c of the pipe sleeve body 121 are configured such that the position of the opening of the second conduit 56 and the position of the opening of the conduit 121c substantially agree with the position of an opening of the ventilation hole 58d of the second sealing member 58 in a fitted state.

By connecting the second port 54 and the second pipe sleeve portion 12 and causing the second port 54 and the second pipe sleeve portion 12 to communicate with each other, a second path is formed. The second path is a path for transmitting a pressure in the abdominal cavity 91 of the patient 90 (see FIG. 1). The pressure measurement conduit 19 shown in FIG. 2 forms a part of the second path. The second tube 4 forms another part of the second path.

The first sealing member 57 is a member which provides sealing between the first port 53 and the first pipe sleeve portion 11 in a fitted state. In the embodiment, the inner peripheral surface 53a of the first port 53 faces a part of the outer peripheral surface 11c of the first pipe sleeve portion 11. The first sealing member 57 is disposed in the first port 53 such that in the fitted state, the first sealing member 57 is positioned between at least a part of the first port 53 and at least a part of the first pipe sleeve portion 11 which overlap with each other, more specifically, between the inner peripheral surface 53a and the outer peripheral surface 11c. It may be also said that the part of the outer peripheral surface 11c is an outer peripheral surface of a part of the first pipe sleeve portion 11 which overlaps with the first port 53. In a state other than the fitted state, the inner diameter of the first sealing member 57 is slightly smaller than the outer diameter of the first pipe sleeve portion 11.

As shown in FIG. 9, in the fitted state, the first sealing member 57 is deformed by receiving external forces from each of the first port 53 and the first pipe sleeve portion 11 which overlap with each other. As a result, because of a restoring force of a material of the first sealing member 57, a first repulsive force F1 is generated from the first sealing member 57 toward each of the first port 53 and the first pipe sleeve portion 11. Because of the first repulsive force F1, the first sealing member 57 is brought into close contact with the first port 53 and the first pipe sleeve portion 11 and hence, sealing is provided between the first port 53 and the first pipe sleeve portion 11.

The second sealing member 58 is a member which provides sealing between the second port 54 and the second pipe sleeve portion 12 in a fitted state. The second sealing member 58 is disposed in the second port 54 such that, in the fitted state, the second sealing member 58 is positioned between the protruding portion 54b of the second port 54 and the pipe sleeve body 121 of the second pipe sleeve portion 12 which push each other.

As shown in FIG. 10, in the fitted state, the second sealing member 58 is deformed by receiving external forces from each of the protruding portion 54b and the pipe sleeve body 121 which push each other. As a result, because of a restoring force of a material of the second sealing member 58, a second repulsive force F2 is generated from the second sealing member 58 toward each of the second port 54 and the second pipe sleeve portion 12. Because of the second repulsive force F2, the second sealing member 58 is brought into close contact with the protruding portion 54b and the pipe sleeve body 121 and hence, sealing is provided between the second port 54 and the second pipe sleeve portion 12.

A compression amount of the second sealing member 58 depends on magnitudes of external forces which the second sealing member 58 receives from each of the protruding portion 54b and the pipe sleeve body 121. A magnitude of the external force depends on a biasing force applied to the pipe sleeve body 121 by the biasing member 122. A magnitude of a biasing force can be adjusted by a length of the protruding portion 54b in the reference direction D, that is, a distance that the protruding portion 54b pushes the pipe sleeve body 121, and a characteristic value of the biasing member 122, more specifically, a spring constant. By adjusting the compression amount of the second sealing member 58, the degree of close contact of the second sealing member 58 with the protruding portion 54b and the pipe sleeve body 121 (hereinafter, referred to as "the degree of close contact of the second sealing member 58") can be adjusted.

In a fitted state, the first tube 3 communicates with the gas feeding conduit 13 (see FIG. 2) connected with the first pipe sleeve portion 11 through the first conduit 55 of the connector 5 and the conduit 11d of the first pipe sleeve portion 11. The second tube 4 communicates with the pressure measurement conduit 19 (see FIG. 2) connected with the second pipe sleeve portion 12 through the second conduit 56 of the connector 5 and the conduit 121c of the pipe sleeve body 121. The connector 5 is provided for connecting the first and second tubes 3, 4 with the first and second pipe sleeve portions 11, 12 such that the first and second tubes 3, 4 respectively communicate with the gas feeding conduit 13 and the pressure measurement conduit 19.

(Manner of Operation and Advantageous Effects)

Next, the manner of operation and advantageous effects of the connector 5 and the insufflation apparatus 1 according to the embodiment are described. In the embodiment, the first and second pipe sleeve portions 11, 12 are mounted on the receptacle 10. The first and second ports 53, 54 are arranged in the connector body 50 of the connector 5, and the first and second tubes 3, 4 are connected with the connector body 50 of the connector 5. The first and second ports 53, 54 communicate with the first and second tubes 3, 4. When the connector body 50 is fitted into the receptacle 10, the first port 53 is connected with and communicates with the first pipe sleeve portion 11, and the second port 54 is connected with and communicates with the second pipe sleeve portion 12. With such a configuration, according to the embodiment, the first and second tubes 3, 4 are connected with the first and second pipe sleeve portions 11, 12 with one handling by way of the connector 5.

According to the embodiment, it is possible to prevent the first and second pipe sleeve portions 11, 12 from being sealed in an incomplete state. Hereinafter the advantageous effect is described in comparison with a connector of a comparison example and an insufflator of the comparison example. The insufflator of the comparison example includes: first and second pipe sleeve portions; and a receptacle on which the first and second pipe sleeve portions are mounted. The respective configurations of the first and second pipe sleeve portions are the same as the configuration of the first pipe sleeve portion 11 in the embodiment. Other components of the insufflator of the comparison example are the same as the corresponding components of the insufflator 2 according to the embodiment.

The connector of the comparison example includes: a connector body fitted into the receptacle of the insufflator of the comparison example; first and second ports formed in the connector body; and first and second sealing members. The respective configurations of the first and second ports are the same as the configuration of the first port 53 according to the embodiment. The respective configurations and the arrangements of the first and second sealing members are the same as the configuration and the arrangement of the first sealing member 57 in the embodiment. More specifically, both the first and second sealing members are formed of an O-shaped ring. Other components of the connector of the comparison example are the same as the corresponding components of the connector 5 according to the embodiment.

In the comparison example, the first sealing member is brought into close contact with the first port and the first pipe sleeve portion thus providing sealing between the first port and the first pipe sleeve portion. In the comparison example, the second sealing member is brought into close contact with the second port and the second port sleeve portion thus providing sealing between the second port and the second pipe sleeve portion.

The respective configurational elements of the connector, the receptacle and the first and second pipe sleeve portions are manufactured within a range of predetermined tolerances in actual manufacturing. Accordingly, even if the connector body is fitted into the receptacle such that a center axis of the first port agrees with a center axis of the first pipe sleeve portion for preventing the first pipe sleeve portion from being sealed in an incomplete state, there is a case that a center axis of the second port is displaced from a center axis of the second pipe sleeve portion. When a displacement amount between the center axes is increased, the second sealing member cannot be brought into close contact with the second port and the second pipe sleeve portion with certainty and hence, the second pipe sleeve portion is sealed in an incomplete state.

Also in the embodiment, even when the connector body 50 is fitted into the receptacle 10 such that the center axis of the first port 53 agrees with the center axis of the first pipe sleeve portion 11 for preventing the first pipe sleeve portion 11 from being sealed in an incomplete state, there is a case where the center axis of the second port 54 and the center axis of the second pipe sleeve portion 12 are displaced from each other. However, in the embodiment, the second port 54 is connected with the second pipe sleeve portion 12 such that the protruding portion 54b of the second port 54 and the pipe sleeve body 121 of the second pipe sleeve portion 12 push each other in the reference direction D. Accordingly, even when the center axis of the protruding portion 54b and the center axis of the pipe sleeve body 121 are displaced from each other, in the same manner as the case where the center axes are not displaced from each other, the connection state can be realized where the protruding portion 54b and the pipe sleeve body 121 push each other. In the embodiment, the second sealing member 58 is positioned between the protruding portion 54b and the pipe sleeve body 121 which push each other. Accordingly, in the embodiment, regardless of the presence or the non-presence of the displacement between the center axis of the protruding portion 54b and the center axis of the pipe sleeve body 121, sealing can be provided between the second port 54 and the second pipe sleeve portion 12 by deforming the second sealing member 58. In this manner, in the embodiment, it is possible to prevent the second pipe sleeve portion 12 from being sealed in an incomplete state while preventing the first pipe sleeve portion 11 from being sealed in an incomplete state.

In the embodiment, the second pipe sleeve portion 12 includes the biasing member 122. Assume a case where the second pipe sleeve portion 12 does not include the biasing member 122 and the pipe sleeve body 121 is fixed to the accommodating member 123, there is a possibility that the second sealing member 58 is not sufficiently deformed due to irregularities in the position of the flange portion 121a of the pipe sleeve body 121 in the reference direction D, irregularities in the length of the protruding portion 54b of the second port 54 in the reference direction D and irregularities in the length of the second sealing member 58 in the reference direction D.

In the embodiment, the configuration is adopted where the biasing member 122 is provided, and the pipe sleeve body 121 is pushed by the protruding portion 54b. With such a configuration, the second sealing member 58 can be deformed with certainty. Accordingly, in the embodiment, it is possible to more effectively prevent the second pipe sleeve portion 12 from being sealed in an incomplete state.

In the embodiment, when the second sealing member 58 receives external forces from each of the protruding portion 54b and the pipe sleeve body 121, the second sealing member 58 is deformed such that the second sealing member 58 is compressed in the reference direction D and expands in a radial direction of the second sealing member 58 (see FIG. 10). When the second sealing member 58 expands in the radial direction, the second sealing member 58 is brought into close contact with the inner peripheral surface of the accommodating hole 123a of the accommodating member 123 and hence, sealing is provided between the second port 54 and the second pipe sleeve portion 12. Accordingly, in the embodiment, it is possible to more effectively prevent the second pipe sleeve portion 12 from being sealed in an incomplete state.

As has been described heretofore, according to the embodiment, the first and second tubes 3, 4 can be connected with the first and second pipe sleeve portions 11, 12 with one handling, and it is possible to prevent the first and second pipe sleeve portions 11, 12 from being sealed in an incomplete state.

Other advantageous effects in the embodiment are described hereinafter. As described previously, in the connector of the comparison example and the insufflator of the comparison example, to prevent the first and second pipe sleeve portions from being sealed in an incomplete state, a following method is conceivable. The first sealing member is brought into close contact with the first port and the first pipe sleeve portion with certainty and the second sealing member is brought into close contact with the second port and the second pipe sleeve portion with certainty by decreasing respective inner diameters of the first and second sealing members (O-shaped rings). However, when the respective inner diameters of the first and second sealing members are decreased, a force necessary for fitting the connector body into the receptacle (hereinafter, referred to as a fitting force) is increased. To reduce such a fitting force, for example, it is necessary to mount a power magnifying mechanism such as a lever mechanism which can obtain a power magnifying effect on the insufflator. In this manner, when the fitting force is increased or the power magnifying mechanism becomes necessary, availability of the insufflator in use is deteriorated for a user. Further, the insufflator becomes expensive by an amount of the power magnifying mechanism.

According to the embodiment, as described previously, it is possible to prevent the first and second pipe sleeve portions 11, 12 from being sealed in an incomplete state and hence, it is unnecessary to decrease the inner diameter of the first sealing member 57 (O-shaped ring) more than necessary. Accordingly, in the embodiment, a fitting force can be reduced compared to the comparison example. Further, in the embodiment, the above-mentioned power magnifying mechanism is unnecessary. From above, according to the embodiment, compared to the comparison example, availability of the insufflator in use can be improved for a user, and a cost of the insufflator 2 can be reduced.

In the embodiment, the flat surface portion 50c2 is formed on the connector body 50. The flat surface portion 10A2 is formed on the fitting hole 10A of the receptacle 10 into which the connector body 50 is inserted. In the embodiment, in fitting the connector body 50 in the receptacle 10, by making the flat surface portions 10A2, 50c2 agree with each other, the posture of the connector body 50 with respect to the receptacle 10 can be simply decided.

When an internal pressure in the second path formed by connecting the second port 54 and the second pipe sleeve portion 12 and causing the second port 54 and the second pipe sleeve portion 12 to communicate with each other is large, it is necessary to increase the degree of close contact of the second sealing member 58 in order to prevent leakage of a gas from between the second port 54 and the second pipe sleeve portion 12. To increase the degree of close contact of the second sealing member 58, it is necessary to adopt the configuration where external forces which the second sealing member 58 receive from each of the protruding portion 54b and the pipe sleeve body 121 are increased. However, with such a configuration, a fitting force is increased.

In the embodiment, the second path is the path for transmitting a pressure in the abdominal cavity 91 of the patient 90, and an internal pressure in the second path is smaller than an internal pressure in the first path which is the path for feeding insufflation gas into the abdominal cavity 91 of the patient 90. With such a configuration, according to the embodiment, compared to the case where the second path is a path for feeding insufflation gas into the abdominal cavity 91 of the patient 90, the degree of close contact of the second sealing member 58 can be decreased and hence, a fitting force can be decreased.

In a fitted state, for causing the second conduit 56 and the conduit 121c of the pipe sleeve body 121 to communicate with each other with certainty, it is desirable that the center axis of the second conduit 56 and the center axis of the conduit 121c agree with each other. However, in an actual operation, there is a case where the center axis of the second conduit 56 and the center axis of the conduit 121c are displaced from each other. In the embodiment, as shown in FIG. 10, the inner diameter of the second conduit 56 is slightly larger than the inner diameter of the conduit 121c. With such a configuration, according to the embodiment, even when the center axis of the second conduit 56 and the center axis of the conduit 121c are displaced from each other, the second conduit 56 and the conduit 121c can be caused to communicate with each other with certainty. The inner diameter of the second conduit 56 may be equal to the inner diameter of the conduit 121c, or may be larger than an inner diameter in the example shown in FIG. 10.

[Modification]

Figure 11:
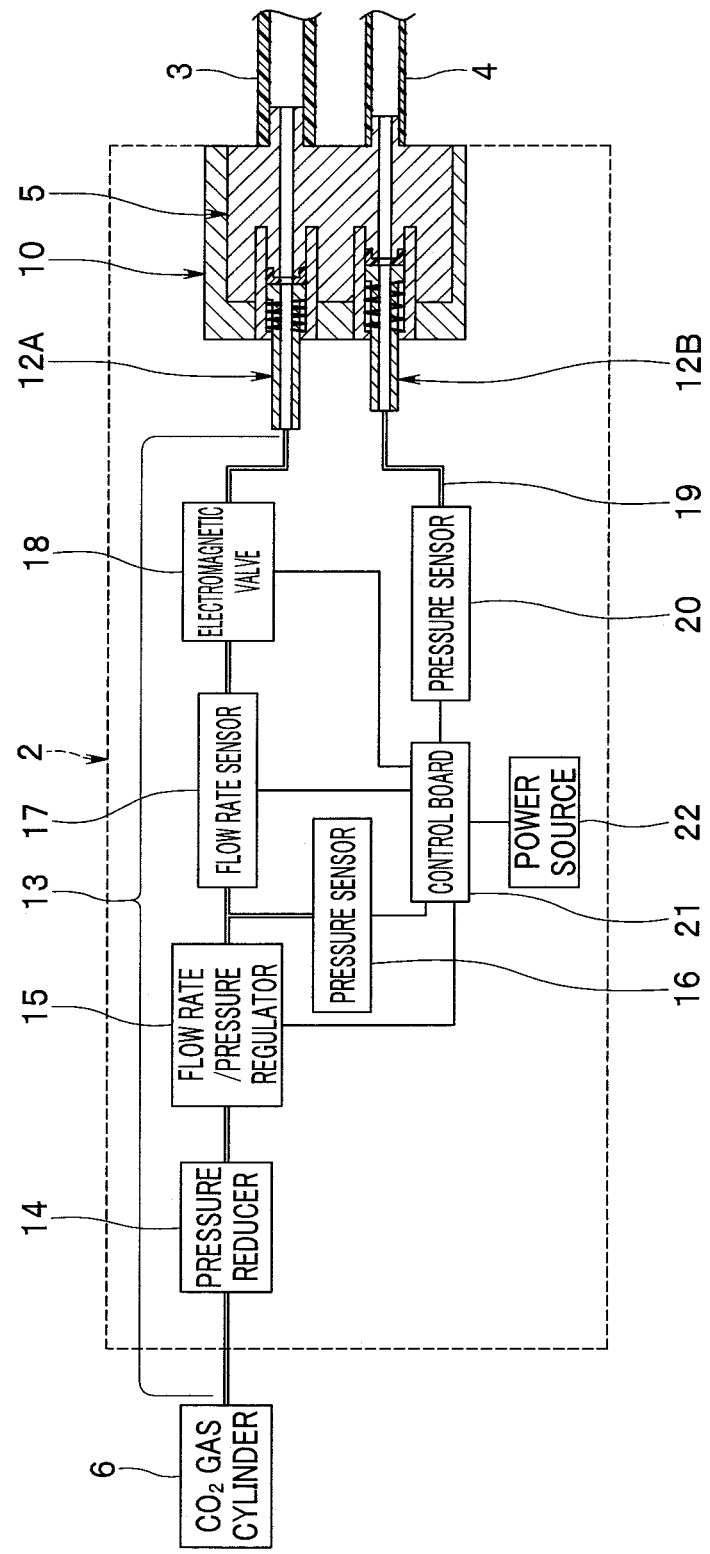
FIG. 11 is an explanatory diagram showing a configuration of a modification of the insufflation apparatus according to the embodiment of the present disclosure.
Figure 12:
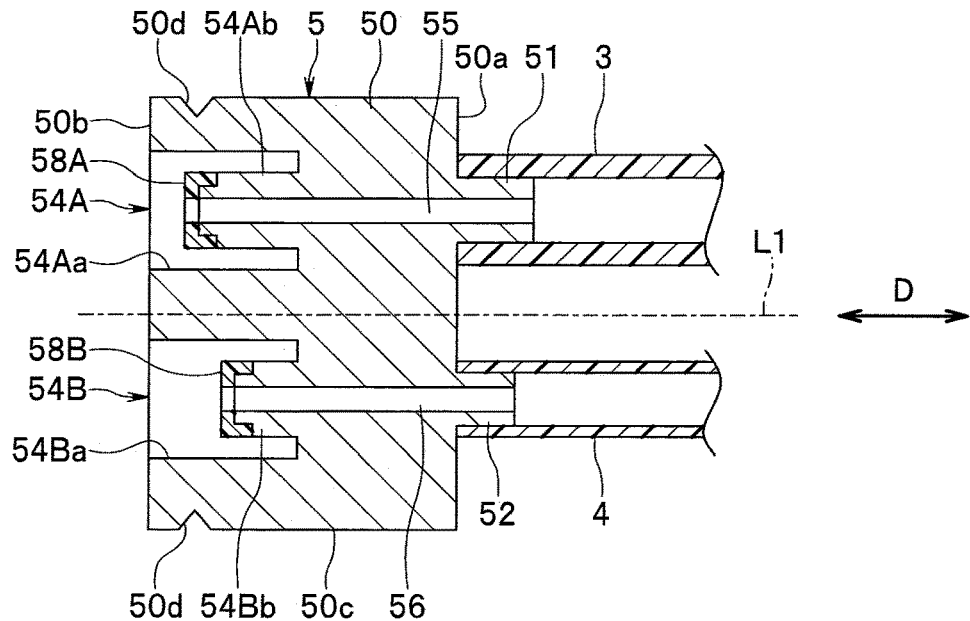
FIG. 12 is a cross-sectional view of a modification of the connector according to the embodiment of the present disclosure.
Figure 13:
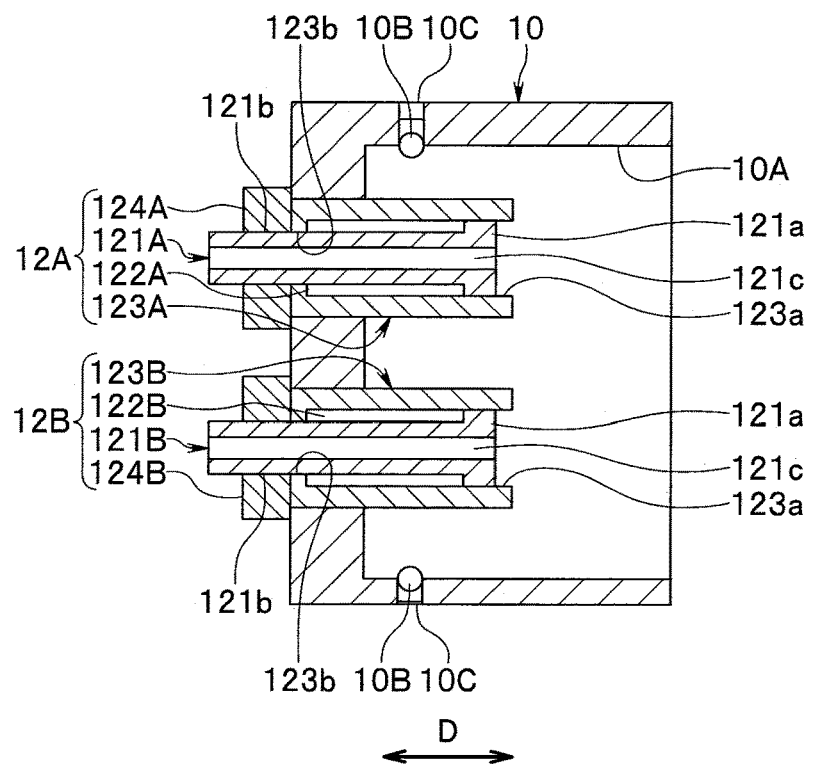
FIG. 13 is a cross sectional view of modifications of the first and second pipe sleeve portions and the receptacle in the embodiment of the present disclosure.

Next, with reference to FIG. 11 to FIG. 13, a modification of the insufflation apparatus 1 in the embodiment is described. FIG. 11 is an explanatory diagram showing a configuration of the modification of the insufflation apparatus 1. FIG. 12 is a cross-sectional view of a modification of the connector 5. FIG. 13 is a cross sectional view of modifications of the first and second pipe sleeve portions and the receptacle 10.

As shown in FIG. 11, in the modification, an insufflator 2 of an insufflation apparatus 1 includes a first pipe sleeve portion 12A and a second pipe sleeve portion 12B in place of the first pipe sleeve portion 11 and the second pipe sleeve portion 12. Other components of the insufflator 2 in the modification are the same as the corresponding components of the insufflator 2 shown in FIG. 2. The first and second pipe sleeve portions 12A, 12B are mounted on a receptacle 10. A gas feeding conduit 13 is connected with the first pipe sleeve portion 12A. A pressure measurement conduit 19 is connected with the second pipe sleeve portion 12B.

(Configuration of Connector)

As shown in FIG. 12, in the modification, a connector 5 includes a first port 54A, a second port 54B, a first sealing member 58A and a second sealing member 58B in place of the first port 53, the second port 54, the first sealing member 57 and the second sealing member 58. The first port 54A is disposed at a position where the first pipe sleeve portion 12A is connected with the first port 54A in a fitted state, and the second port 54B is disposed at a position where the second pipe sleeve portion 12B is connected with the second port 54B in the fitted state.

The respective configurations of the first and second ports 54A, 54B are the same as the configuration of the second port 54. In other words, as shown in FIG. 12, the first port 54A includes: a groove portion 54Aa formed on a second end portion 50b of a connector body 50 by cutting; and a protruding portion 54Ab protruding from a bottom portion of the groove portion 54Aa such that the protruding portion 54Ab extends in a reference direction D. The shapes of the groove portion 54Aa and the protruding portion 54Ab are the same as the shapes of the groove portion 54a and the protruding portion 54b shown in FIG. 3 and FIG. 4. A stepped portion for attaching the first sealing member 58A is formed on a distal end of the protruding portion 54Ab.

As shown in FIG. 12, the second port 54B includes: a groove portion 54Ba formed on the second end portion 50b of the connector body 50 by cutting; and a protruding portion 54Bb protruding from a bottom portion of the groove portion 54Ba such that the protruding portion 54Bb extends in the reference direction D. The shapes of the groove portion 54Ba and the protruding portion 54Bb are the same as the shapes of the groove portion 54a and the protruding portion 54b shown in FIG. 3 and FIG. 4. A stepped portion for attaching the second sealing member 58B is formed on a distal end of the protruding portion 54Bb.

As shown in FIG. 12, a length of the protruding portion 54Ab in the reference direction D is larger than a length of the protruding portion 54Bb in the reference direction D.

In the modification, one end of a first conduit 55 opens at the distal end of the protruding portion 54Ab of the first port 54A, and the other end of the first conduit 55 opens at a distal end of a first connecting portion 51. With such a configuration, the first port 54A communicates with a first tube 3. One end of the second conduit 56 opens at the distal end of the protruding portion 54Bb of the second port 54B, and the other end of the second conduit 56 opens at a distal end of a second connecting portion 52. With such a configuration, a second port 54B communicates with a second tube 4.

In a fitted state, the first port 54A is connected with and communicates with the first pipe sleeve portion 12A, and the second port 54B is connected with and communicates with the second pipe sleeve portion 12B. The first sealing member 58A provides sealing between the first port 54A and the first pipe sleeve portion 12A in the fitted state. The second sealing member 58B provides sealing between the second port 54B and the second pipe sleeve portion 12B in the fitted state.

The first sealing member 58A is mounted on the distal end of the protruding portion 54Ab of the first port 54A. The second sealing member 58B is mounted on the distal end of the protruding portion 54Bb of the second port 54B. Respective materials of the first and second sealing members 58A, 58B are the same as a material of the second sealing member 58.

The respective shapes of the first and second sealing members 58A, 58B are the same as the shape of the second sealing member 58 shown in FIG. 5. In other words, the first and second sealing members 58A, 58B each have: a first surface 58a and a second surface 58b which are directed toward sides opposite to each other; a fitting hole 58c which opens in the first surface 58a; and a ventilation hole 58d which is continuously formed with the fitting hole 58c, and opens in the second surface 58b.

(Configurations of First and Second Pipe Sleeve Portions)

The arrangement of the first and second pipe sleeve portions 12A, 12B in the receptacle 10 are the same as the arrangement of the first and second pipe sleeve portions 11, 12. The respective materials of the first and second pipe sleeve portions 12A, 12B are the same as the material of the second pipe sleeve portion 12.

The respective configurations of the first and second pipe sleeve portions 12A, 12B are the same as the configuration of the second pipe sleeve portion 12. In other words, as shown in FIG. 13, the first pipe sleeve portion 12A includes: a pipe sleeve body 121A movably disposed in the reference direction D; a biasing member 122A applying a biasing force to the pipe sleeve body 121A in the reference direction D; an accommodating member 123A accommodating the pipe sleeve body 121A and the biasing member 122A; and a removal preventing member 124A. As shown in FIG. 13, the biasing member 122A is a spring, and more specifically, a coil spring.

As shown in FIG. 13, the second pipe sleeve portion 12B includes: a pipe sleeve body 121B movably disposed in the reference direction D; a biasing member 122B applying a biasing force to the pipe sleeve body 121B in the reference direction D; an accommodating member 123B accommodating the pipe sleeve body 121B and the biasing member 122B; and a removal preventing member 124B. As shown in FIG. 13, the biasing member 122B is a spring, and more specifically, a coil spring.

The respective configurations of the pipe sleeve bodies 121A, 121B are the same as the configuration of the pipe sleeve body 121 shown in FIG. 6. In other words, the pipe sleeve bodies 121A, 121B each have a flange portion 121a, a tubular portion 121b and a conduit 121c. The conduit 121c of the pipe sleeve body 121A communicates with a fitting hole 10A of a receptacle 10 and the gas feeding conduit 13 (see FIG. 11). The conduit 121c of the pipe sleeve body 121B communicates with the fitting hole 10A and the pressure measurement conduit 19 (see FIG. 11).

The respective configurations of the accommodating members 123A, 123B are the same as the configuration of the accommodating member 123 shown in FIG. 6. In other words, the accommodating members 123A, 123B each have a cylindrical shape extending in the reference direction D. The accommodating members 123A, 123B are fixed to the receptacle 10 such that a part of each of the accommodating members 123A, 123B is positioned in the fitting hole 10A. The accommodating members 123A, 123B each have an accommodating hole 123a and a passing hole 123b. Between the accommodating hole 123a and the passing hole 123b, a stepped portion formed by difference in respective inner diameters of the accommodating hole 123a and the passing hole 123b exists.

The pipe sleeve body 121A is inserted into the accommodating hole 123a and the passing hole 123b of the accommodating member 123A. The pipe sleeve body 121A is movable in the accommodating hole 123a of the accommodating member 123A in the reference direction D. The biasing member 122A (coil spring) is accommodated in the accommodating hole 123a of the accommodating member 123A, and is sandwiched between the flange portion 121a of the pipe sleeve body 121A and the stepped portion of the accommodating member 123A. The tubular portion 121b of the pipe sleeve body 121A is inserted into the biasing member 122A (coil spring).

The pipe sleeve body 121B is inserted into the accommodating hole 123a of the accommodating member 123B and the passing hole 123b. The pipe sleeve body 121B is movable in the accommodating hole 123a of the accommodating member 123B in the reference direction D. The biasing member 122B (coil spring) is accommodated in the accommodating hole 123a of the accommodating member 123B, and is sandwiched between the flange portion 121a of the pipe sleeve body 121B and the stepped portion of the accommodating member 123B. The tubular portion 121b of the pipe sleeve body 121B is inserted into the biasing member 122B (coil spring).

The removal preventing member 124A is fixed to the tubular portion 121b of the pipe sleeve body 121A outside the receptacle 10. The removal preventing member 124A has a function of preventing the removal of the pipe sleeve body 121A from the accommodating member 123A. The removal preventing member 124B is fixed to the tubular portion 121b of the pipe sleeve body 121B outside the receptacle 10. The removal preventing member 124B has a function of preventing the removal of the pipe sleeve body 121B from the accommodating member 123B.

(Fitted State)

Figure 14:
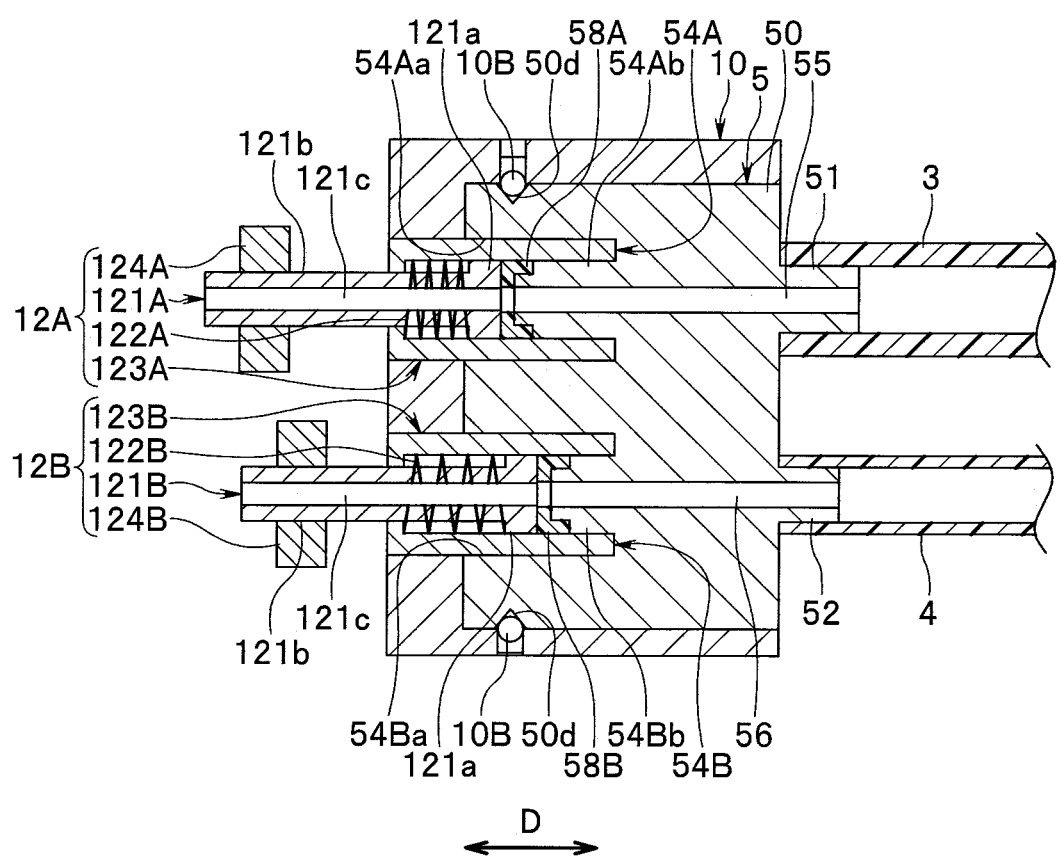
FIG. 14 is a cross-sectional view showing a state where the connector shown in FIG. 12 engages with the receptacle shown in FIG. 13 by fitting.

Next, with reference to FIG. 12 to FIG. 14, the fitted state in the modification is described. FIG. 14 is a cross-sectional view showing the fitted state in the modification. As described previously, the first port 54A is connected with and communicates with the first pipe sleeve portion 12A. A method of connecting the first port 54A and the first pipe sleeve portion 12A with each other is substantially the same as the method of connecting the second port 54 and the second pipe sleeve portion 12 with each other described with reference to FIG. 8 and FIG. 10. By replacing the second port 54, the groove portion 54a, the protruding portion 54b, the second pipe sleeve portion 12, the pipe sleeve body 121, the biasing member 122, the accommodating member 123 and the second sealing member 58 in the description of the method of connecting the second port 54 and the second pipe sleeve portion 12 with each other, respectively with the first port 54A, the groove portion 54Aa, the protruding portion 54Ab, the first pipe sleeve portion 12A, the pipe sleeve body 121A, the biasing member 122A, the accommodating member 123A and the first sealing member 58A, the method of connecting the first port 54A and the first pipe sleeve portion 12A with each other is described.

As described previously, the second port 54B is connected with and communicates with the second pipe sleeve portion 12B. The method of connecting the second port 54B and the second pipe sleeve portion 12B with each other is substantially the same as the method of connecting the second port 54 and the second pipe sleeve portion 12 with each other described with reference to FIG. 8 and FIG. 10. By replacing the second port 54, the groove portion 54a, the protruding portion 54b, the second pipe sleeve portion 12, the pipe sleeve body 121, the biasing member 122, the accommodating member 123 and the second sealing member 58 in the description of the method of connecting the second port 54 and the second pipe sleeve portion 12 with each other, respectively with the second port 54B, the groove portion 54Ba, the protruding portion 54Bb, the second pipe sleeve portion 12B, the pipe sleeve body 121B, the biasing member 122B, the accommodating member 123B and the second sealing member 58B, the method of connecting the second port 54B and the second pipe sleeve portion 12B with each other is described.

In the modification, particularly, the protruding portion 54Ab of the first port 54A inserted into the accommodating hole 123a of the accommodating member 123A of the first pipe sleeve portion 12A pushes the pipe sleeve body 121A of the first pipe sleeve portion 12A, and the protruding portion 54Bb of the second port 54B inserted into the accommodating hole 123a of the accommodating member 123B of the second pipe sleeve portion 12B pushes the pipe sleeve body 121B of the second pipe sleeve portion 12B. As described previously, a length of the protruding portion 54Ab in the reference direction D is larger than a length of the protruding portion 54Bb in the reference direction D. Accordingly, as shown in FIG. 14, a distance that the protruding portion 54Ab pushes the pipe sleeve body 121A becomes larger than a distance that the protruding portion 54Bb pushes the pipe sleeve body 121B. As a result, a compression amount of the biasing member 122A in the reference direction D becomes larger than a compression amount of the biasing member 122B in the reference direction D, and a biasing force applied to the pipe sleeve body 121A by the biasing member 122A becomes larger than a biasing force applied to the pipe sleeve body 121B by the biasing member 122B.

The first sealing member 58A is a member which provides sealing between the first port 54A and the first pipe sleeve portion 12A in a fitted state. A method which provides sealing between the first port 54A and the first pipe sleeve portion 12A by the first sealing member 58A is substantially the same as the method which provides sealing between the second port 54 and the second pipe sleeve portion 12 by the second sealing member 58 described with reference to FIG. 8 and FIG. 10. By replacing the second port 54, the protruding portion 54b, the second pipe sleeve portion 12, the pipe sleeve body 121, the biasing member 122 and the second sealing member 58 in the description of the method which provides sealing between the second port 54 and the second pipe sleeve portion 12 by the second sealing member 58, respectively with the first port 54A, the protruding portion 54Ab, the first pipe sleeve portion 12A, the pipe sleeve body 121A, the biasing member 122A and the first sealing member 58A, the method which provides sealing between the first port 54A and the first pipe sleeve portion 12A by the first sealing member 58A is described.

The second sealing member 58B is a member which provides sealing between the second port 54B and the second pipe sleeve portion 12B in a fitted state. A method which provides sealing between the second port 54B and the second pipe sleeve portion 12B by the second sealing member 58B is substantially the same as the method which provides sealing between the second port 54 and the second pipe sleeve portion 12 by the second sealing member 58 described with reference to FIG. 8 and FIG. 10. By replacing the second port 54, the protruding portion 54b, the second pipe sleeve portion 12, the pipe sleeve body 121, the biasing member 122 and the second sealing member 58 in the description of the method which provides sealing between the second port 54 and the second pipe sleeve portion 12 by the second sealing member 58, respectively with the second port 54B, the protruding portion 54Bb, the second pipe sleeve portion 12B, the pipe sleeve body 121B, the biasing member 122B and the second sealing member 58B, the method which provides sealing between the second port 54B and the second pipe sleeve portion 12B by the second sealing member 58B is described.

As described previously, in the modification, the distance that the protruding portion 54Ab pushes the pipe sleeve body 121A is larger than the distance that the protruding portion 54Bb pushes the pipe sleeve body 121B, and a biasing force applied to the pipe sleeve body 121A by the biasing member 122A becomes larger than a biasing force applied to the pipe sleeve body 121B by the biasing member 122B. Accordingly, a compression amount of the first sealing member 58A becomes larger than a compression amount of the second sealing member 58B. As a result, the degree of close contact of the first sealing member 58A with the protruding portion 54Ab and the pipe sleeve body 121A (hereinafter, referred to as the degree of close contact of the first sealing member 58A) becomes larger than the degree of close contact of the second sealing member 58B with the protruding portion 54Bb and the pipe sleeve body 121B (hereinafter, referred to as the degree of close contact of the second sealing member 58B).

In the modification, the first path is formed by connecting the first port 54A and the first pipe sleeve portion 12A and causing the first port 54A and the first pipe sleeve portion 12A to communicate with each other, and the second path is formed by connecting the second port 54B and the second pipe sleeve portion 12B and causing the second port 54B and the second pipe sleeve portion 12B to communicate with each other. The first path, the first path is a path for supplying insufflation gas into the abdominal cavity 91 of the patient 90 (see FIG. 1). The second path is a path for transmitting a pressure in the abdominal cavity 91 of the patient 90. An internal pressure of the first path becomes larger than an internal pressure of the second path. Assume a case where the degree of close contact of the first sealing member 58A is smaller than the degree of close contact of the second sealing member 58B, there is a concern that the gas leaks from between the first port 54A and the first pipe sleeve portion 12A. To prevent such a leakage, when the degree of close contact of the first sealing member 58A is increased, a fitting force is increased.

In the modification, the degree of close contact of the first sealing member 58A is larger than the degree of close contact of the second sealing member 58B. In other words, in the modification, by correlating an inner pressure of the path and the degree of close contact with each other such that, when the internal pressure of the path where the sealing member is used is large, the degree of close contact of the sealing member becomes large, it is possible to reduce a fitting force while preventing a leakage of a gas from between the first port 54A and the first pipe sleeve portion 12A.

In the modification, a spring constant of the biasing member 122A and a spring constant of the biasing member 122B may be equal to each other or may be different from each other. Further, by setting a length of the protruding portion 54Ab in the reference direction D and a length of the protruding portion 54Bb in the reference direction D equal to each other, and by making the spring constant of the biasing member 122A and the spring constant of the biasing member 122B different from each other, a compression amount of the first sealing member 58A and a compression amount of the second sealing member 58B may be set different from each other. In this case, it is preferable to regulate the spring constant of the biasing member 122A and the spring constant of the biasing member 122B such that a compression amount of the first sealing member 58A becomes larger than a compression amount of the second sealing member 58B.

In the modification, the biasing members 122A, 122B are provided in the first and second pipe sleeve portions 12A, 12B respectively. Assume a case where the biasing members 122A, 122B are not provided in the first and second pipe sleeve portions 12A, 12B respectively, and the pipe sleeve bodies 121A, 121B are fixed to the accommodating members 123A, 123B respectively. In this case, there is a possibility that the first and second sealing members 58A, 58B are not sufficiently deformed due to irregularities in positions of respective flange portions 121a of the pipe sleeve bodies 121A, 121B in the reference direction D, irregularities in respective lengths of the protruding portions 54Ab, 54Bb in the reference direction D, or irregularities in respective lengths of the first and second sealing members 58A, 58B in the reference direction D.

In the modification, the configuration is adopted where the biasing members 122A, 122B are provided, the pipe sleeve body 121A is pushed by the protruding portion 54Ab, and the pipe sleeve body 121B is pushed by the protruding portion 54Bb, the first and second sealing members 58A, 58B can be deformed with certainty. Accordingly, it is possible to prevent the first and second pipe sleeve portions 12A, 12B from being incompletely sealed.

The present disclosure is not limited to the above-mentioned embodiment, and various alterations, modifications and the like are conceivable within a range that the gist of the present disclosure is not changed. For example, an O-shaped ring may be used in place of the second sealing member 58 shown in FIG. 5. The O-shaped ring is attached to the distal end of the protruding portion 54b.

In the case where a supply amount of insufflation gas is relatively small, the second path formed by connecting the second port 54 and the second pipe sleeve portion 12 and causing the second port 54 and the second pipe sleeve portion 12 to communicate with each other may form a path for transmitting a pressure in the abdominal cavity 91 of the patient 90, and the first path formed by connecting the first port 53 and the first pipe sleeve portion 11 and causing the first port 53 and the first pipe sleeve portion 11 to communicate with each other may form a path for supplying insufflation gas to the abdominal cavity 91 of the patient 90.

Both the first path and the second path may be supply paths for feeding insufflation gas. In this case, a larger amount of insufflation gas can be supplied to the abdominal cavity 91 of the patient 90, and the insufflation apparatus 1 can be applied to the abdominal cavity 91 having a larger volume. An internal pressure in the first path may be equal to an internal pressure of the second path, or may be larger than the internal pressure of the second path. In the latter case, it is possible to reduce a fitting force while preventing a leakage of a gas from between the first port 53 and the first pipe sleeve portion 11.

In the modification, the ports, the pipe sleeve portions and the sealing members are provided in two sets. However, the ports, the pipe sleeve portions and the sealing members may be provided in three or more sets. With such a configuration, three or more tubes can be connected with one touch.

What is claimed is:

1. A connector for an insufflator, the connector being configured to be inserted into a receptacle provided in the insufflator, the connector comprising:
    a first port that is configured to be connected to and in communication with a first pipe sleeve portion mounted on the receptacle of the insufflator when the connector is inserted into the receptacle of the insufflator, the first pipe sleeve portion including a pipe sleeve surface configured to receive an external force in a direction orthogonal to an insertion direction of the connector, the first port including a port surface configured to receive the external force in the direction orthogonal to the insertion direction of the connector, the first port being configured to be connected to the first pipe sleeve portion such that at least part of the first port engages with and overlaps at least part of the first pipe sleeve portion;
    a second port that is configured to be connected to and in communication with a second pipe sleeve portion, which is: (i) provided in the receptacle, and (ii) includes a pipe sleeve body including a pipe sleeve distal end surface configured to receive an external force in a direction parallel to the insertion direction of the connector, the pipe sleeve body being biased in a direction opposite to the insertion direction of the connector into the receptacle, when the connector is inserted into the receptacle of the insufflator, the second port including a port distal end surface configured to receive the external force in the direction parallel to the insertion direction of the connector, the second port being configured to be connected with the second pipe sleeve portion such that at least part of the second port and at least part of the second pipe sleeve portion engage with each other and push each other;
    a first sealing member that is:
        disposed in the first port such that the first sealing member is positioned between the first port and the first pipe sleeve portion when the connector is inserted into the receptacle of the insufflator, and configured to provide sealing between the first port and the first pipe sleeve portion; and
    a second sealing member that is:
        disposed in the second port such that the second sealing member is positioned between the port distal end surface of the second port and the pipe sleeve distal end surface of the pipe sleeve body of the second pipe sleeve portion when the connector is inserted into the receptacle of the insufflator, and
        elastically deformable such that, when the connector is inserted into the receptacle of the insufflator, the second sealing member is compressed in the direction parallel to the insertion direction of the connector and expanded in the direction orthogonal to the insertion direction of the connector to provide sealing between the second port and the second pipe sleeve portion.

2. The connector according to claim 1, wherein:
    the at least part of the first port extends in a reference direction which is parallel to an imaginary straight line,
    the second port is configured to be connected with the second pipe sleeve portion such that the at least part of the second port and the at least part of the second pipe sleeve portion engage with each other and push each other in the reference direction,
    the first sealing member is positioned between the at least part of the first port and the at least part of the first pipe sleeve portion which engage with and overlap each other, and
    the second sealing member is positioned between the at least part of the second port and the at least part of the second pipe sleeve portion which engage with and push each other.

3. The connector according to claim 1, wherein:
    the first port includes:
        as the port surface, an inner peripheral surface that is configured to face an outer peripheral surface of the at least part of the first pipe sleeve portion when the connector is inserted into the receptacle of the insufflator; and
        a groove portion formed on the inner peripheral surface in a circumferential direction about a center axis of the inner peripheral surface, and
    the first sealing member has an annular shape, and a part of the first sealing member is accommodated in the groove portion.

4. The connector according to claim 1, wherein the first sealing member is made of an elastically deformable material.

5. The connector according to claim 1, wherein:
    the second port includes a protruding portion including the port distal end surface, and
    the second sealing member is mounted on the port distal end surface.

6. The connector according to claim 1, wherein:
    the first port is configured to be connected to and in communication with the first pipe sleeve portion so as to form a first path for supplying insufflation gas to an abdominal cavity of a patient, and
    the second port is configured to be connected to and in communication with the second pipe sleeve portion so as to form a second path for transmitting a pressure in the abdominal cavity.

7. The connector according to claim 1, wherein:
    the second pipe sleeve portion further includes an accommodating member having an accommodating hole,
    the pipe sleeve body is inserted into the accommodating hole,
    the second sealing member is disposed in the second port such that the second sealing member is inserted into the accommodating hole when the connector is inserted into the receptacle of the insufflator, and
    an outer diameter of the second sealing member is smaller than an inner diameter of the accommodating hole.

8. The connector according to claim 7, wherein the second sealing member is elastically deformable such that, when the connector is inserted into the receptacle of the insufflator, the second sealing member is expanded in the direction orthogonal to the insertion direction of the connector to be in close contact with the inner peripheral surface of the accommodating hole of the accommodating member, thereby providing the sealing between the second port and the second pipe sleeve portion.

9. An insufflation apparatus comprising:
an insufflator including a first pipe sleeve portion, a second pipe sleeve portion and a receptacle on which the first pipe sleeve portion and the second pipe sleeve portion are mounted;
a first tube and a second tube configured to communicate with an inside of an abdominal cavity of a patient; and
a connector for connecting the first tube and the second tube with the first pipe sleeve portion and the second pipe sleeve portion, respectively, the connector including:
 a connector body including a first end portion and a second end portion which are positioned on sides opposite to each other, the connector body being configured to be inserted into and engage the receptacle of the insufflator in a fitted state;
 a first connecting portion and a second connecting portion that are: (i) disposed on a first end portion side of the connector body, and (ii) connected with the first tube and the second tube, respectively;
 a first port disposed on a second end portion side of the connector body, the first port communicating with the first tube, the first port including a port surface configured to receive an external force in a direction orthogonal to an insertion direction of the connector body in the fitted state, the first port being connected with and communicating with the first pipe sleeve portion in the fitted state;
 a second port disposed on the second end portion side of the connector body, the second port communicating with the second tube, the second port including a port distal end surface configured to receive an external force in a direction parallel to the insertion direction of the connector body in the fitted state, the second port being connected with and communicating with the second pipe sleeve portion in the fitted state;
 a first sealing member providing sealing between the first port and the first pipe sleeve portion in the fitted state; and
 a second sealing member providing sealing between the second port and the second pipe sleeve portion in the fitted state,
wherein:
 the first port is connected with the first pipe sleeve portion in the fitted state such that at least a part of the first port extending in a reference direction overlaps with at least a part of the first pipe sleeve portion extending in the reference direction, the reference direction being parallel to an imaginary straight line that is orthogonal to the first end portion and the second end portion, and
 the second port is connected with the second pipe sleeve portion in the fitted state such that at least part of the second port and at least part of the second pipe sleeve portion push each other in the reference direction,
 the first pipe sleeve portion includes a pipe sleeve surface configured to receive the external force in the direction orthogonal to the insertion direction of the connector body in the fitted state,
 the second pipe sleeve portion includes a pipe sleeve body including a pipe sleeve distal end surface configured to receive the external force in the direction parallel to the insertion direction of the connector body in the fitted state,
 the first sealing member is disposed in the first port such that the first sealing member is positioned between at least part of the first port and at least part of the first pipe sleeve portion which overlap with each other in the fitted state, and
 the second sealing member is:
  disposed in the second port such that the second sealing member is positioned between the port distal end surface of the second port and the pipe sleeve distal end surface of the pipe sleeve body of the second pipe sleeve portion which push each other in the fitted state, and
  elastically deformable such that, in the fitted state, the second sealing member is compressed in the direction parallel to the insertion direction of the connector and expanded in the direction orthogonal to the insertion direction of the connector to provide the sealing between the second port and the second pipe sleeve portion.

10. The insufflation apparatus according to claim 9, wherein:
the first port includes:
 an inner peripheral surface that: (i) faces an outer peripheral surface of the at least part of the first pipe sleeve portion in the fitted state, and (ii) includes a center axis parallel to the reference direction; and
 a groove portion formed on the inner peripheral surface in a circumferential direction about the center axis, and
the first sealing member has an annular shape, and a part of the first sealing member is accommodated in the groove portion.

11. The insufflation apparatus according to claim 9, wherein:
the first sealing member is made of an elastically deformable material, and
in the fitted state, the first sealing member is deformed by external forces exerted by each of the first port and the first pipe sleeve portion, and provides sealing between the first port and the first pipe sleeve portion by a first repulsive force generated from the first sealing member toward each of the first port and the first pipe sleeve portion.

12. The insufflation apparatus according to claim 9, wherein:
the second port includes a protruding portion including the port distal end surface and extending in the reference direction, and
the second sealing member is mounted on the port distal end surface.

13. The insufflation apparatus according to claim 9, wherein:
in the fitted state, the second sealing member is deformed by external forces exerted by each of the second port and the second pipe sleeve portion, and generates a second repulsive force toward each of the second port and the second pipe sleeve portion to provide further sealing between the second port and the second pipe sleeve portion.

14. The insufflation apparatus according to claim 9, wherein:
the second pipe sleeve portion includes:
 a pipe sleeve body movably disposed in the reference direction; and
 a biasing member configured to apply a biasing force to the pipe sleeve body in the reference direction, and
in the fitted state, at least a part of the second port is configured to push the pipe sleeve body in a pushing direction, and the biasing member is configured to apply a biasing force to the pipe sleeve body in a direction opposite to the pushing direction.

15. The insufflation apparatus according to claim 14, wherein the biasing member is a spring.

16. The insufflation apparatus according to claim 9, wherein:
   the first port is connected with and communicates with the first pipe sleeve portion in the fitted state to form a first path for supplying insufflation gas into the abdominal cavity,
   the second port is connected with and communicates with the second pipe sleeve portion in the fitted state to form a second path for transmitting a pressure in the abdominal cavity, and
   the insufflator further includes:
      a gas feeding conduit forming a part of the first path and supplying the insufflation gas;
      a pressure sensor; and
      a pressure measurement conduit forming a part of the second path and communicating with the pressure sensor.

17. The insufflation apparatus according to claim 9, wherein the second pipe sleeve portion further includes a biasing member that is configured to apply a biasing force to the pipe sleeve body in the reference direction so as to bias the second pipe sleeve portion in the direction opposite to the insertion direction.

18. The insufflation apparatus according to claim 9, wherein:
   the second pipe sleeve portion further includes an accommodating member having an accommodating hole,
   the pipe sleeve body is inserted into the accommodating hole,
   the second sealing member is inserted into the accommodating hole in the fitted state, and
   an outer diameter of the second sealing member is smaller than an inner diameter of the accommodating hole.

19. The insufflation apparatus according to claim 18, wherein the second sealing member is elastically deformable such that, in the fitted state, the second sealing member is expanded in the direction orthogonal to the insertion direction of the connector to be in close contact with the inner peripheral surface of the accommodating hole of the accommodating member, thereby providing the sealing between the second port and the second pipe sleeve portion.

* * * * *